United States Patent
Iio et al.

(10) Patent No.: US 9,446,206 B2
(45) Date of Patent: Sep. 20, 2016

(54) PHARMACEUTICAL INJECTION DEVICE

(75) Inventors: Toshiaki Iio, Ehime (JP); Yukihiro Takabatake, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 636 days.

(21) Appl. No.: 13/821,765

(22) PCT Filed: Nov. 14, 2011

(86) PCT No.: PCT/JP2011/006346
§ 371 (c)(1),
(2), (4) Date: Mar. 8, 2013

(87) PCT Pub. No.: WO2012/066767
PCT Pub. Date: May 24, 2012

(65) Prior Publication Data
US 2013/0172819 A1    Jul. 4, 2013

(30) Foreign Application Priority Data
Nov. 18, 2010   (JP) .................................. 2010-257588

(51) Int. Cl.
*A61M 5/50* (2006.01)
*A61M 5/20* (2006.01)
(Continued)

(52) U.S. Cl.
CPC ............. *A61M 5/5086* (2013.01); *A61M 5/20* (2013.01); *A61M 5/34* (2013.01); *A61M 2005/206* (2013.01); *A61M 2005/2407* (2013.01); *A61M 2005/2488* (2013.01); *A61M 2205/14* (2013.01)

(58) Field of Classification Search
CPC ...... A61M 5/20; A61M 5/34; A61M 5/5086; A61M 2005/2006; A61M 2205/14; A61M 2005/2488; A61M 2005/206; A61M 2005/2407

USPC ........................................................ 604/111
See application file for complete search history.

(56) References Cited

U.S. PATENT DOCUMENTS 5,681,285 A * 10/1997 Ford ..................... A61M 5/172
                                                              604/151
7,621,850 B2   11/2009 Piaget et al.
(Continued)

FOREIGN PATENT DOCUMENTS

CN    1663626    9/2005
CN    1864757    11/2006
(Continued)

OTHER PUBLICATIONS

Office Action issued Jul. 2, 2014 in corresponding Chinese Application No. CN201180048481.8, with English translation.
(Continued)

*Primary Examiner* — Theodore Stigell
*Assistant Examiner* — Amber Stiles
(74) *Attorney, Agent, or Firm* — Wenderoth, Lind & Ponack, L.L.P.

(57) ABSTRACT

A pharmaceutical injection device (100) comprises a main body (1), a movable member (11), a pharmaceutical holding member (10), and a first detector (28). The movable member (11) is mounted movably in the lengthwise direction of the main body (1). The pharmaceutical holding member (10) is mounted to the movable member (11), has a needle mount (17) for an injection needle (16) on one end, and houses a pharmaceutical syringe (50) containing the drug to be injected into a body. The first detector (28) is provided to the movable member (11) and detects the mounting of the needle (16) on the needle mount (17). The pharmaceutical injection device (100) improves the accuracy of detecting the mounting of a needle and/or a pharmaceutical syringe.

14 Claims, 26 Drawing Sheets

(51) Int. Cl.
*A61M 5/34* (2006.01)
*A61M 5/24* (2006.01)

(56) References Cited

U.S. PATENT DOCUMENTS

| | | | |
|---|---|---|---|
| 7,704,231 | B2 | 4/2010 | Pongpairochana et al. |
| 7,967,784 | B2 | 6/2011 | Pongpairochana et al. |
| 8,002,674 | B2 | 8/2011 | Piaget et al. |
| 8,206,351 | B2 | 6/2012 | Sugimoto et al. |
| 8,376,985 | B2 | 2/2013 | Pongpairochana et al. |
| 8,550,962 | B2 | 10/2013 | Piaget et al. |
| 8,696,524 | B2 | 4/2014 | Piaget et al. |
| 8,734,300 | B2 | 5/2014 | Piaget et al. |
| 2004/0214693 | A1 | 10/2004 | Piaget et al. |
| 2005/0197650 | A1 | 9/2005 | Sugimoto et al. |
| 2006/0270986 | A1* | 11/2006 | Hommann .......... A61M 5/2033 604/136 |
| 2007/0197968 | A1* | 8/2007 | Pongpairochana ..... A61M 5/20 604/131 |
| 2009/0054832 | A1* | 2/2009 | Sugimoto ............... A61M 5/20 604/67 |
| 2009/0062777 | A1 | 3/2009 | Sugimoto et al. |
| 2009/0156931 | A1* | 6/2009 | Nemoto ............ A61M 5/14546 600/432 |
| 2010/0075812 | A1 | 3/2010 | Piaget et al. |
| 2010/0160857 | A1 | 6/2010 | Pongpairochana et al. |
| 2011/0004165 | A1 | 1/2011 | Iio et al. |
| 2011/0201998 | A1 | 8/2011 | Pongpairochana et al. |
| 2011/0257602 | A1 | 10/2011 | Watanabe et al. |
| 2011/0312472 | A1 | 12/2011 | Piaget et al. |
| 2013/0190138 | A1 | 7/2013 | Piaget et al. |
| 2013/0190139 | A1 | 7/2013 | Piaget et al. |
| 2014/0336009 | A1 | 11/2014 | Piaget et al. |
| 2015/0359977 | A1 | 12/2015 | Watanabe et al. |
| 2015/0374912 | A1 | 12/2015 | Sugimoto et al. |

FOREIGN PATENT DOCUMENTS

| | | |
|---|---|---|
| CN | 1921899 | 2/2007 |
| EP | 2 361 647 | 8/2011 |
| JP | 2005-245852 | 9/2005 |
| JP | 2005-287676 | 10/2005 |
| JP | 2007-509659 | 4/2007 |
| JP | 2007-522853 | 8/2007 |
| JP | 2007-313372 | 12/2007 |
| JP | 2007-313373 | 12/2007 |
| WO | 2004/078270 | 9/2004 |
| WO | 2005/077441 | 8/2005 |
| WO | 2008/007674 | 1/2008 |
| WO | 2009/125582 | 10/2009 |
| WO | 2009/140782 | 11/2009 |
| WO | 2010/073452 | 7/2010 |

OTHER PUBLICATIONS

International Search Report issued Feb. 7, 2012 in International (PCT) Application No. PCT/JP2011/006346.
Office Action issued Mar. 23, 2015 in corresponding Chinese Application No. 201180048481.8, with English translation.
English translation of the Extended European Search Report issued Mar. 8, 2016 in corresponding European Application No. 11841451.5.
Notice of Allowance issued May 31, 2016 in corresponding Japanese patent application No. 2012-544109.

* cited by examiner

PHARMACEUTICAL INJECTION DEVICE

TECHNICAL FIELD

The present invention relates to a pharmaceutical injection device.

BACKGROUND ART

FIG. 26 shows an example of the configuration (partial cross section) of a conventional pharmaceutical injection device. The pharmaceutical injection device 900 shown in FIG. 26 comprises a main body case 902 to which a cap 901 is removably attached, a cartridge mount 903 provided inside the main body case 902, and a cartridge mounting detector 904. The main body case 902 is mounted to the cartridge mount 903, and holds in its interior a pharmaceutical syringe 907 filled with a drug 906 to be injected into a body. An injection needle mount 908 for injecting the drug 906 into a body is provided on the front end side of the main body case 902. The mounting detector 904 is provided near the rear end of the cartridge mount 903, and detects the mounting of the pharmaceutical syringe 907 (see Patent Literature 1, for example).

With the above-mentioned conventional pharmaceutical injection device 900, first the pharmaceutical syringe 907 is inserted into the main body case 902, after which a needle is mounted on the front end side of the pharmaceutical syringe 907.

At this point the mounting detector 904 detects whether or not the pharmaceutical syringe 907 has been mounted inside the main body case 902, and thereby detects the mounting of the pharmaceutical syringe 907.

In FIG. 26, the injection needle is shown in a state of not yet having been mounted, and during actual use, the cap 901 is removed to mount the injection needle.

CITATION LIST

Patent Literature

Patent Literature 1: Japanese Laid-Open Patent Application 2007-313373

SUMMARY

Technical Problem

With the above-mentioned conventional pharmaceutical injection device 900, once the pharmaceutical syringe 907 and a needle have been mounted to the main body case, they are fixed inside the main body case. Thus, after mounting there is no change in the positional relation between the main body case and the pharmaceutical syringe 907 to which the needle has been mounted.

However, the following problems are encountered with a pharmaceutical injection device of a type with which an inner case is further provided for mounting a pharmaceutical cartridge inside the main body case. In this case, the inner case is mounted to the main body case, and then the inner case can move according to an injection operation, a needle removal operation, etc.

When the pharmaceutical cartridge is mounted to the inner case and the inner case is placed in the pharmaceutical injection device, a mounting detector provided to the main body case (provided on the stationary side) detects when the inner case is mounted along with its mounted pharmaceutical cartridge. However, there is the possibility that the inner case will further move after having been mounted. If this happens, the mounting of a needle or a pharmaceutical cartridge, and the positions thereof, cannot be detected accurately. Another problem is that changes over time caused by movement of the inner case adversely affect the accuracy of detection by the mounting detector.

In view of this, it is an object of the present invention to improve accuracy in the detection of the mounting of a needle and/or pharmaceutical syringe.

Solution to Problem

In one aspect of the present invention, the pharmaceutical injection device comprises a main body, a movable member, a pharmaceutical holding member, and a first detector. The movable member is mounted movably in a lengthwise direction of the main body. The pharmaceutical holding member is mounted to the movable member, includes a needle mount for an injection needle on one end, and is configured to house a pharmaceutical syringe containing a drug to be injected into a body. The first detector is provided to the movable member and configured to detect a mounting of an injection needle on the needle mount.

Advantageous Effects

It is an object of the present invention to improve accuracy in the detection of the mounting of a needle and/or pharmaceutical syringe.

DESCRIPTION OF EMBODIMENTS

Embodiments of the present invention will be described in detail through reference to the drawings.

1. Embodiment 1

1.1. Configuration of Pharmaceutical Injection Device 100

Figure 1:
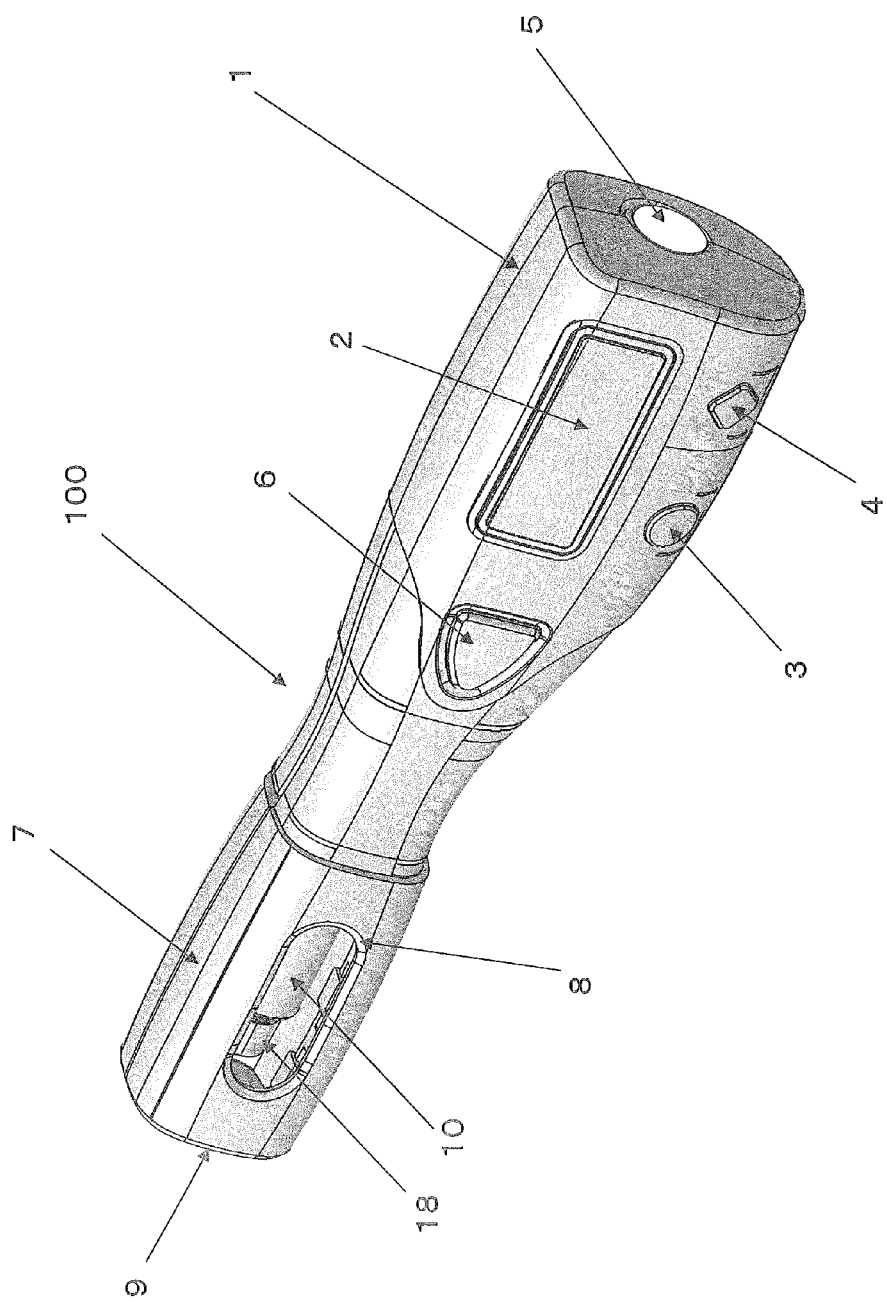
FIG. 1 is an oblique view of the exterior of the pharmaceutical injection device pertaining to Embodiment 1.

FIG. 1 is a view of the exterior of the pharmaceutical injection device 100 pertaining to Embodiment 1, which is an example of the present invention.

As shown in FIG. 1, the pharmaceutical injection device 100 comprises a main body case 1 (an example of a device main body) and a cap 7 that is removably mounted on the front end side of the main body case 1.

The main body case 1 has on its outside a display component 2, an air venting button 3, an end button 4, a power button 5, and a pharmaceutical injection button 6. The display component 2 is disposed on the front face side of the main body case 1. The air venting button 3 and the end button 4 are disposed near the display component 2. The power button 5 is disposed at the rear end of the main body case 1 (the end on the opposite side from the cap 7). The pharmaceutical injection button 6 is disposed to one side of the display component 2 on the front face side of the main body case 1.

The cap 7 is removably mounted on the distal end side of the main body case 1. A confirmation window 8 is provided on the front face side of the cap 7, and an opening 9 is provided at the distal end.

As shown in FIG. 1, the confirmation window 8 is formed so that the interior of the cap 7 can be seen, and a syringe holder 10 mounted in the cap 7 can also be seen. The syringe holder 10, as will be discussed below, has a needle 16 mounted on its front end side (see FIG. 3), and has a needle cap 18 that protects the needle 16.

Figure 2:
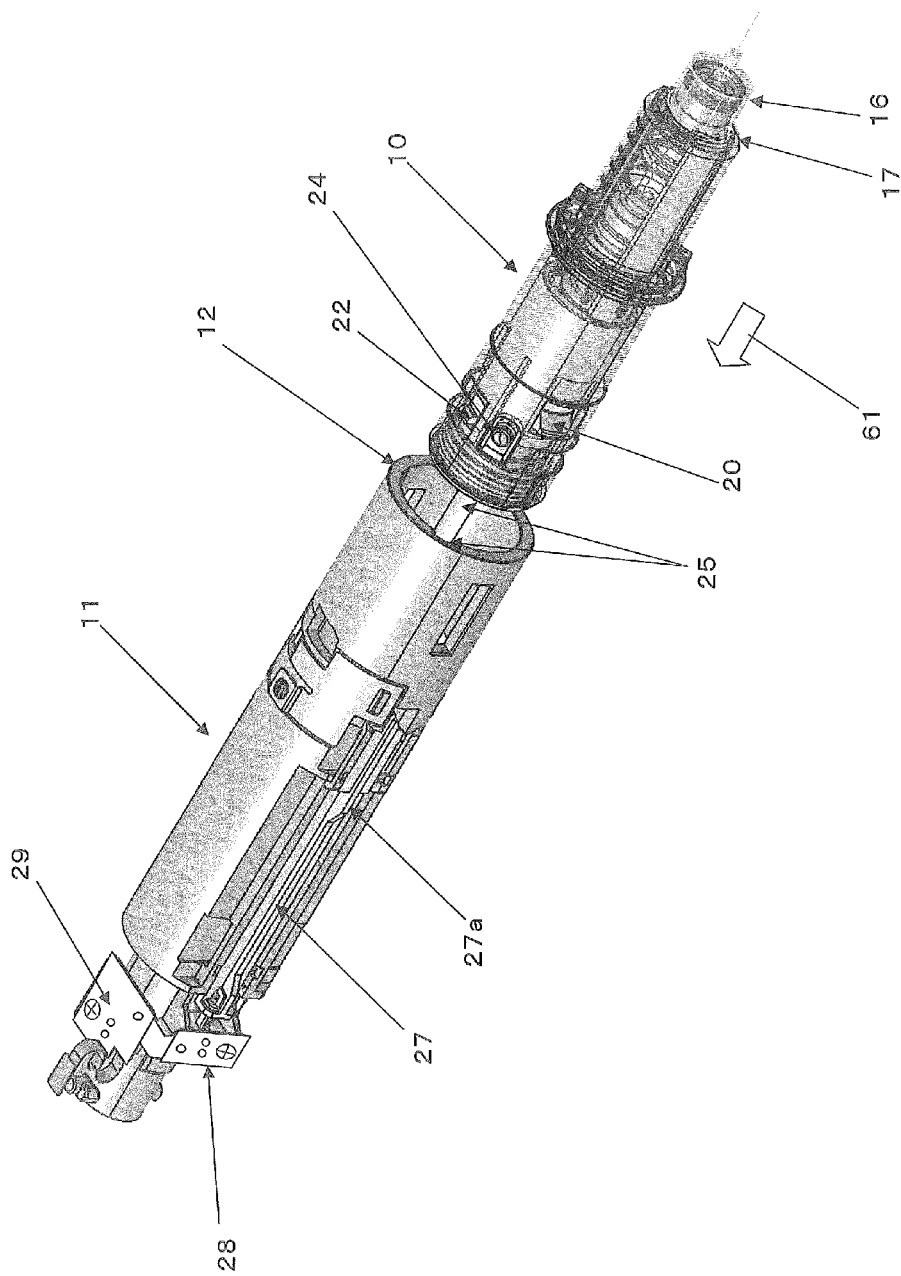
FIG. 2 is an oblique view of the movable portion in the interior of this pharmaceutical injection device.
Figure 11:
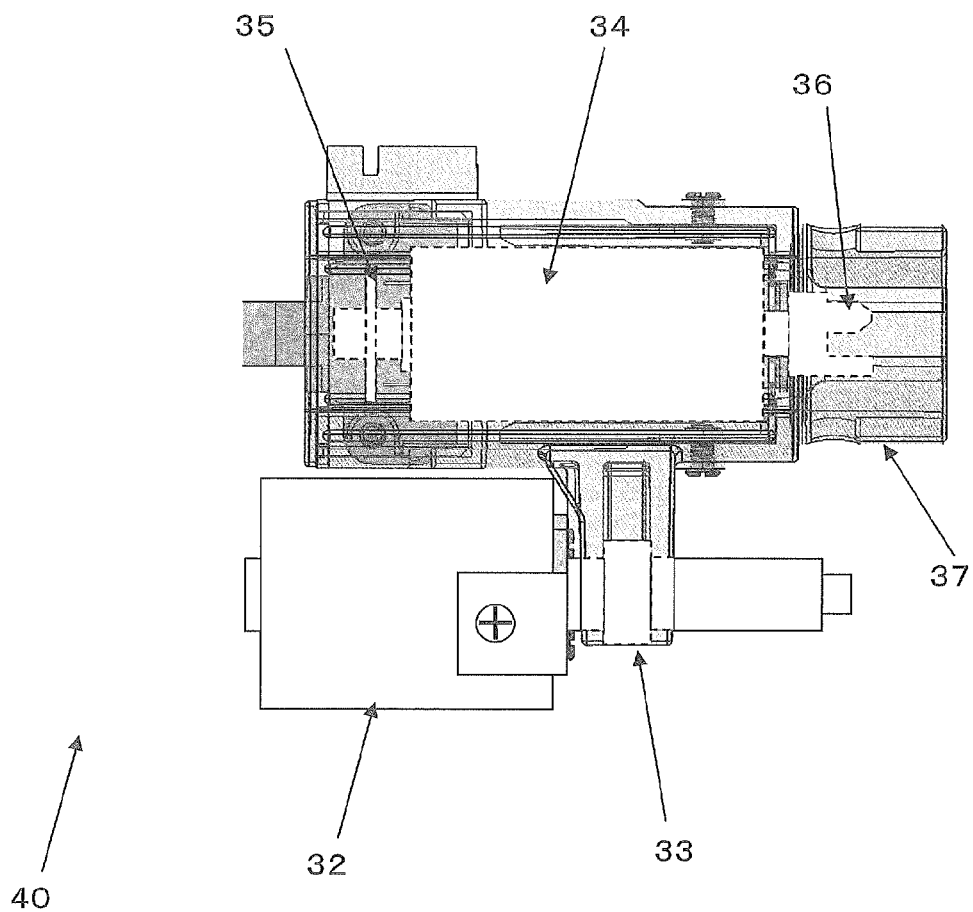
FIG. 11 is a diagram of the motor of the pharmaceutical injection device.

As shown in FIG. 2, the pharmaceutical injection device 100 further comprises an inner case 11 (an example of a movable member) mounted inside the main body case 1, the syringe holder 10 (an example of a pharmaceutical holding member) mounted on the front end side of the inner case 11, a detecting sensor 28 (an example of a first detector), a detecting sensor 29 (an example of a second detector), and a motor 40 (an example of a driver; see FIG. 11). The syringe holder 10 is mounted by being inserted in the direction of the arrow 61 in FIG. 2 into the inner case 11. The detecting sensor 28 detects the mounting state between the inner case 11 and the syringe holder 10 to which the needle 16 is mounted. The motor 40 drives the piston and drives the needle for insertion and withdrawal. The various portions of the pharmaceutical injection device 100 will be described in detail.

1.1.1. Syringe Holder 10

FIGS. 3 to 7 show the configuration of the syringe holder 10 and the constituent members thereof.

Figure 3:
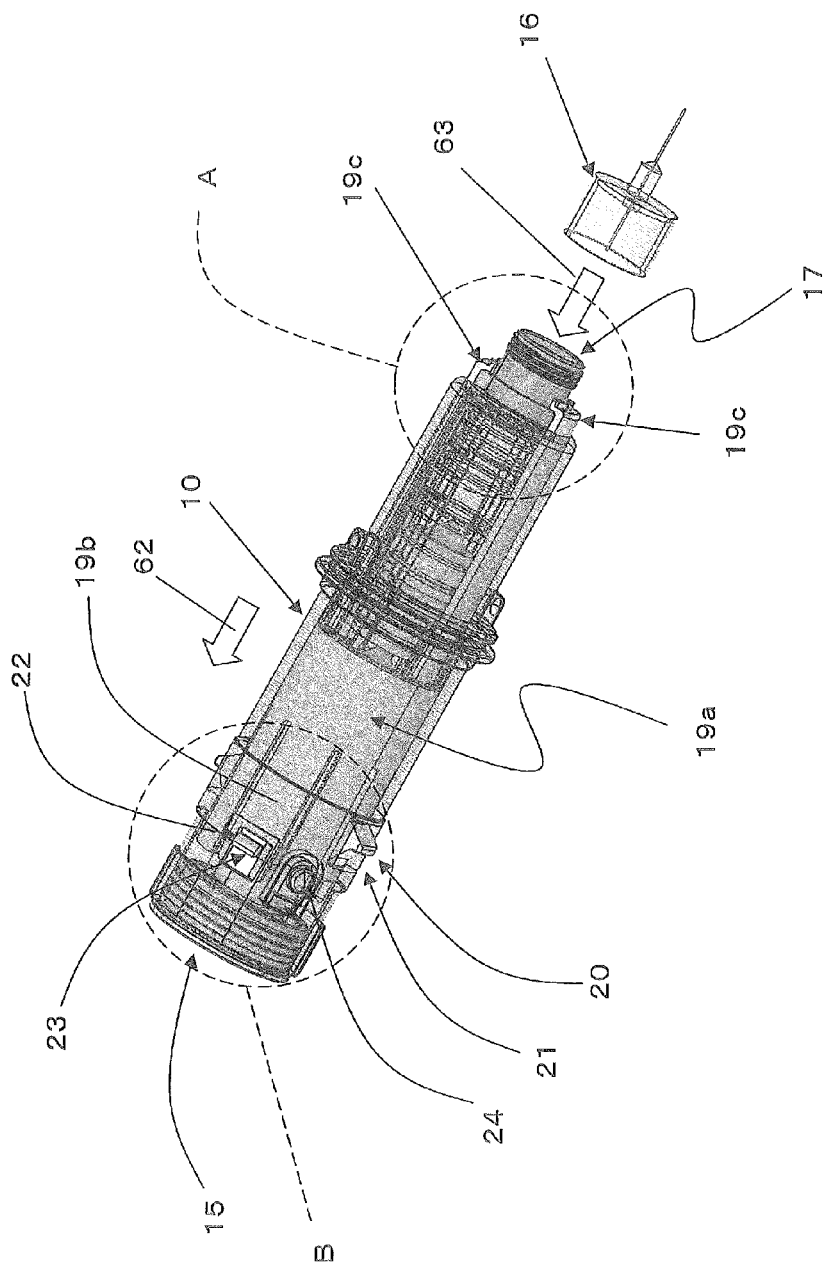
FIG. 3 is an oblique view of a syringe holder of this pharmaceutical injection device.
Figure 4:
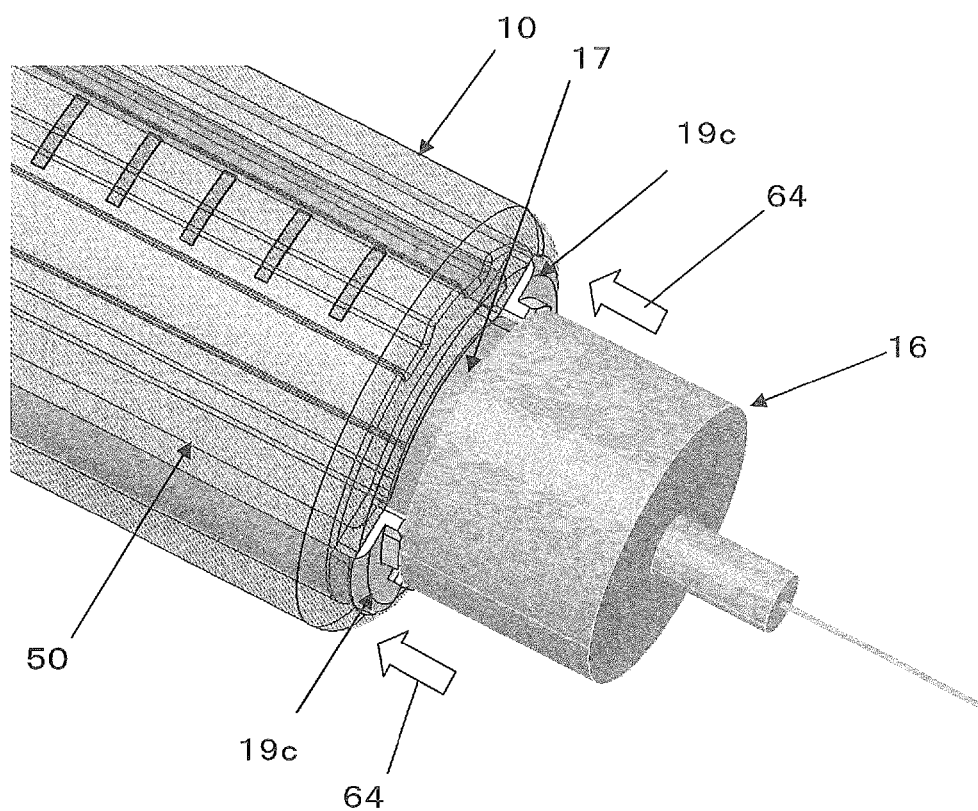
FIG. 4 is a detail view of the main components of the syringe holder.
Figure 5:
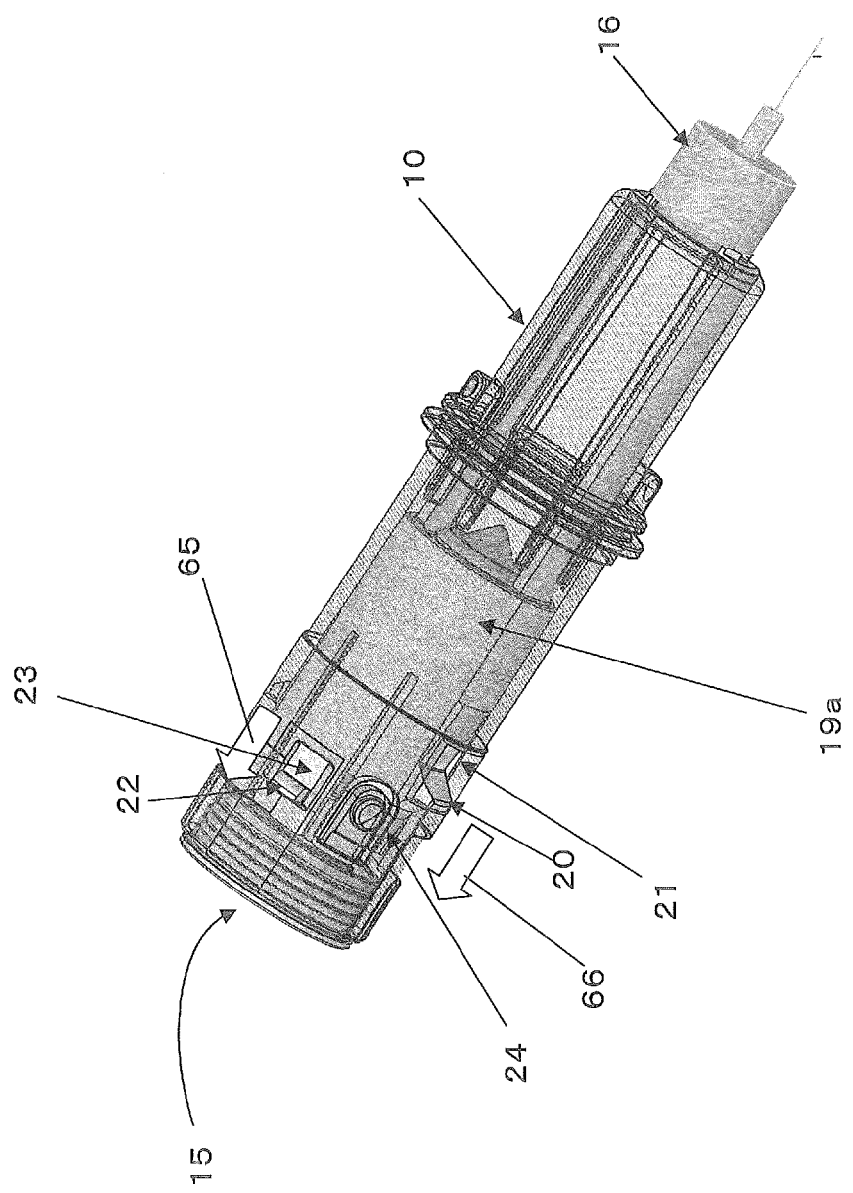
FIG. 5 is a diagram of the syringe holder when a needle has been mounted.
Figure 6:
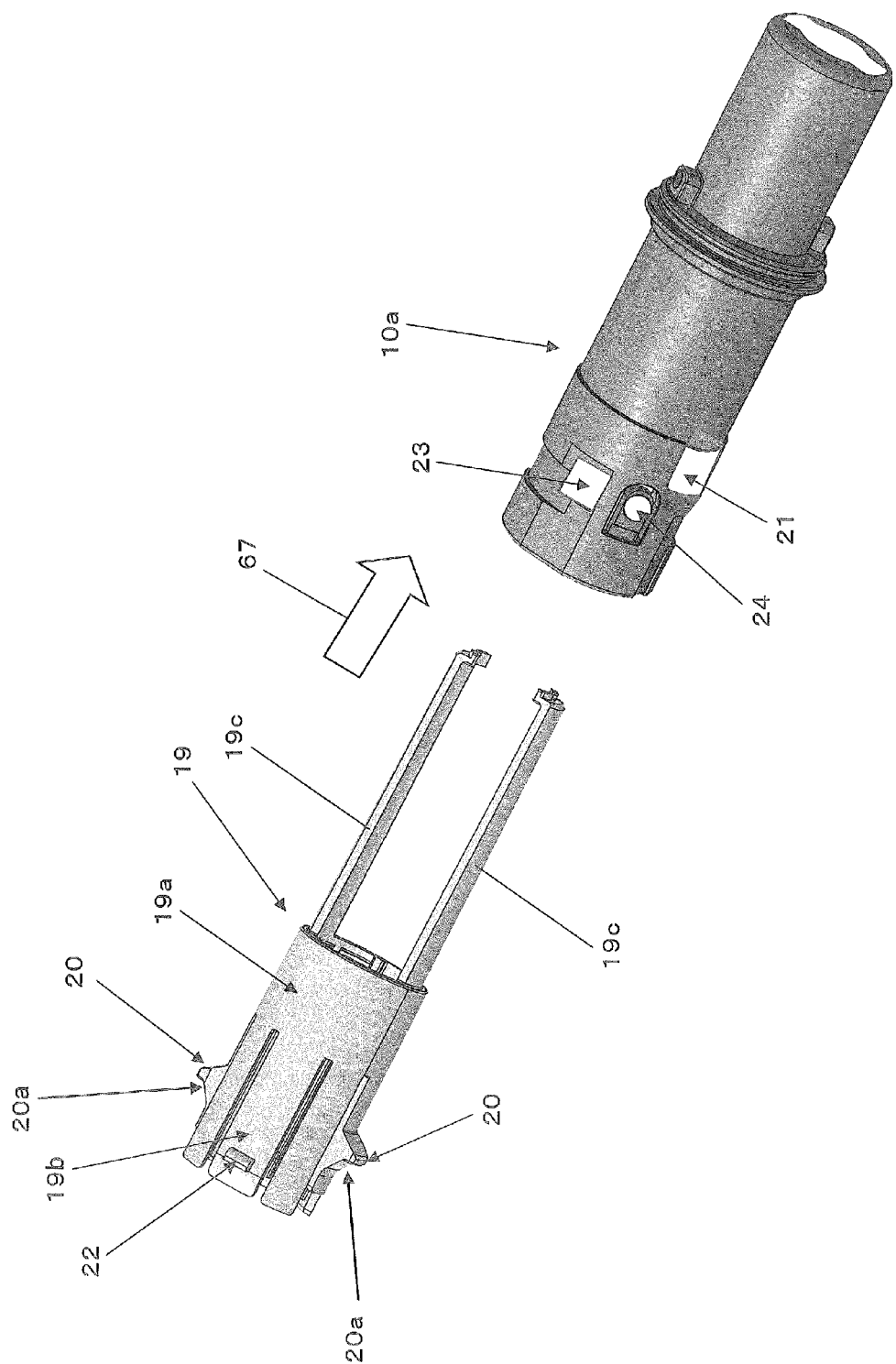
FIG. 6 is an exploded view of the syringe holder.
Figure 7:
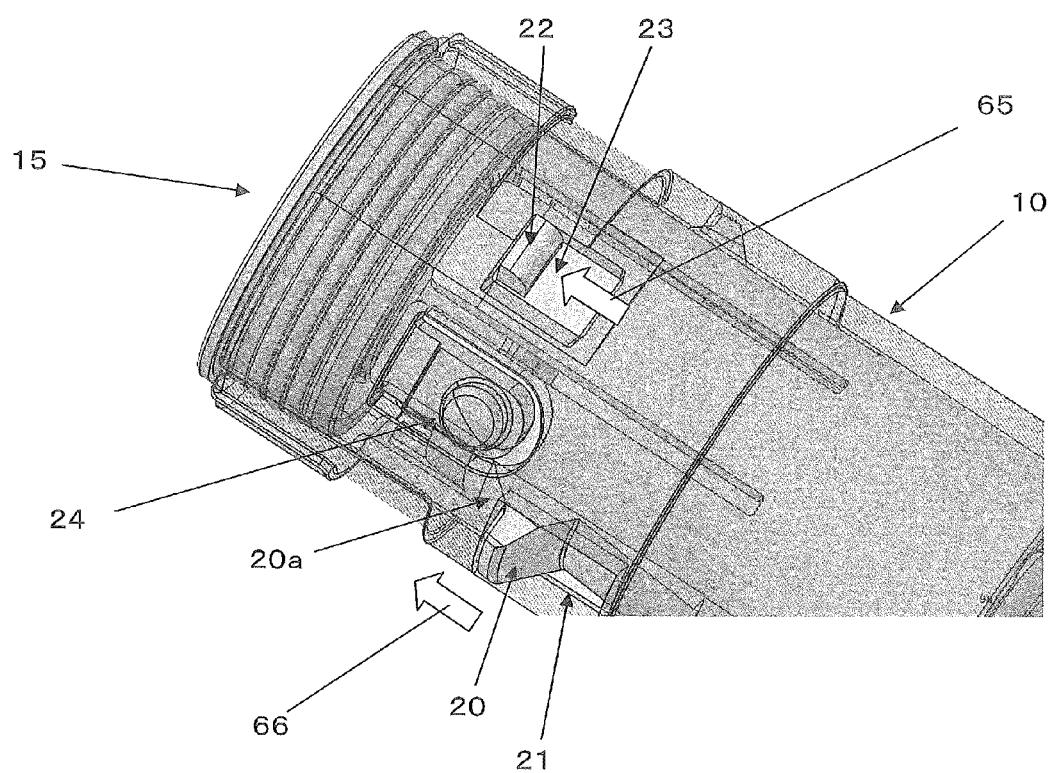
FIG. 7 is a detail view of the main components of the syringe holder.

FIG. 3 shows the entire syringe holder 10 and the needle 16. FIG. 4 is a detail view of the front end portion of the syringe holder 10 (the part A within the dotted line in FIG. 3), and in particular a needle mount 17 and its surrounding portion. FIG. 5 shows the syringe holder 10 in a state in which the needle 16 has been mounted, and shows the state of a detector rod 19 (an example of a detection member or a first detection member) for detecting the mounting of the needle. FIG. 6 is an exploded view of the syringe holder 10. FIG. 7 is a detail view of the rear end portion of the syringe holder 10 (the part B within the dotted line in FIG. 3), and in particular a piston insertion opening 15 and its surrounding portion.

In FIGS. 3 to 5, the needle cap 18 (see FIG. 1) is not mounted to the needle 16 to facilitate understanding, but in actual practice the mounting of the needle 16 to the needle mount 17 is performed in a state in which the needle cap 18 has been mounted to the needle 16 for the sake of safety.

As shown in FIG. 3, the syringe holder 10 has the needle mount 17 on its front end side, and has on its rear end side the piston insertion opening 15 into which the front end side of a piston 14 (see FIG. 12) is inserted. A pharmaceutical syringe 50 that contains a drug is mounted inside the syringe holder 10. The needle mount 17 may instead be provided to one end of the pharmaceutical syringe 50.

As shown in FIGS. 3 and 4, the detector rod 19 (an example of a needle mounting confirmation means; see FIG. 6) is provided near the needle mount 17 of the syringe holder 10 so that its front end side is exposed. As shown in FIG. 3, the detector rod 19 extends through the inside of the syringe holder 10 to the rear side (the piston insertion opening 15 side). Protrusions 20 stick out from the syringe holder 10 through openings 21 in the syringe holder 10 on the rear end side of the detector rod 19.

The detector rod 19 will now be described in further detail. As shown in FIG. 6, the syringe holder 10 comprises a cylindrical syringe holder cover 10a and the detector rod 19 that is housed in the interior of the syringe holder cover 10a and is disposed slidably. The detector rod 19 has a rod main body 19a and two prongs 19c extending from the rod main body 19a, and the distal ends of these 19c are bent so as to face each other.

Meanwhile, the rod main body 19a of the detector rod 19 has a cylindrical shape, and four extensions 19b are provided extending from the cylindrical portion all the way to the rear end, spaced apart by approximately 90 degrees.

Thus, the protrusions 20 are provided to one opposing pair of the four extensions 19b provided at a 90-degree spacing, and protrusions 22 for detecting the mounting of a needle are provided to the other opposing pair. The protrusions 22 are formed so as to stick out of the syringe holder 10 through openings 23 in the syringe holder cover 10a (here, a pair is provided at opposing positions) when the detector rod 19 has been mounted to the syringe holder cover 10a. Similarly, the protrusions 20 are configured so as to stick out of the syringe holder 10 through the openings 21 in the syringe holder cover 10a (here, a pair is provided at opposing positions; see FIG. 5).

A spring (not shown) is provided to the rear end of the syringe holder 10, and the two pairs of extensions 19b are biased to the front end side by the spring. As a result, as shown in FIGS. 3 and 4, the distal ends of the prongs 19c of the detector rod 19 are exposed near the needle mount 17.

As shown in FIGS. 3 and 4, when the needle 16 is mounted to the needle mount 17, the distal end of the detector rod 19 is pressed rearward (the direction of the arrow 64) by the needle 16. As a result, as shown in FIGS. 5 and 7, the protrusions 20 move to the rear end of the openings 21 (move in the direction of the arrow 66). The rear end side (piston insertion opening 15 side) of the protrusions 20 has an inclined face 20a that decreases in height toward the rear end side. As the protrusions 20 move to the rear end side of the detector rod 19, they move rearward (in the direction of the arrow 66 in FIG. 5). The inclined faces 20a move rearward (in the direction of the arrow 66 in FIG. 7) while in contact with the rear ends of the openings 21. Consequently, as discussed above, the protrusions 20 move to the rear ends within the openings 21 and are substantially recessed into the syringe holder 10.

When the detector rod 19 is further slid in the direction of the arrow 65 shown in FIG. 7, the protrusions 22 slide in the direction of the arrow 65 in a state of sticking out from the syringe holder 10. At this point the protrusions 22 protrude only slightly through the openings 23 to the outside of the syringe holder 10.

Therefore, when the rear end side of the syringe holder 10 is inserted through a syringe holder mounting opening 12 of the inner case 11 as shown in FIG. 2, the protrusions 20 of the syringe holder 10 and the protrusions 22 of the detector rod 19 do not hit the opening edges of the syringe holder mounting opening 12 and impede this insertion.

As shown in FIG. 7, opposing protrusions 24 disposed at a 180-degree spacing are provided to the outer surface of the rear end of the syringe holder 10. Meanwhile, as shown in FIG. 2, grooves 25 (provided at opposing positions within the inner case 11) that extend rearward from the syringe holder mounting opening 12 are provided inside the inner case 11. When the rear end side of the syringe holder 10 is inserted through the syringe holder mounting opening 12 of the inner case 11, the protrusions 24 slide rearward along these grooves 25.

1.1.2. Inner Case 11

Figure 8:
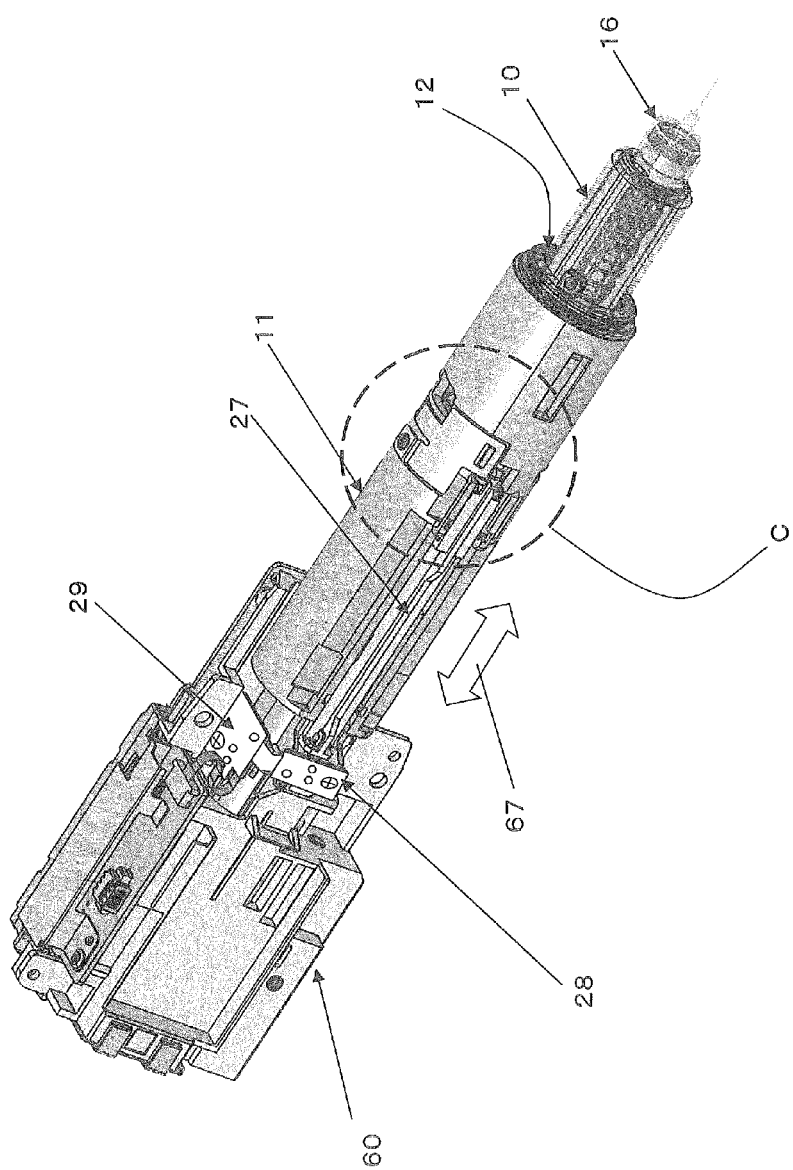
FIG. 8 is a diagram of the inner case when it has been attached to part of the pharmaceutical injection device.

As shown in FIG. 8, the inner case 11 is provided slidably in the arrow 67 direction with respect to a main frame 60 that is fixed in the interior of the main body case 1. The inner case 11 comprises a detecting lever 27 (an example of a second detection member) that extends in the lengthwise direction and is exposed on the outside. The detecting lever 27 has a reinforcing plate 27a (see FIG. 9) formed at the thick-walled part on the outer surface of the front end side (syringe holder mounting opening side) of the detecting lever 27.

1.1.3 Mounting of Syringe Holder 10 and Inner Case 11

Figure 9:
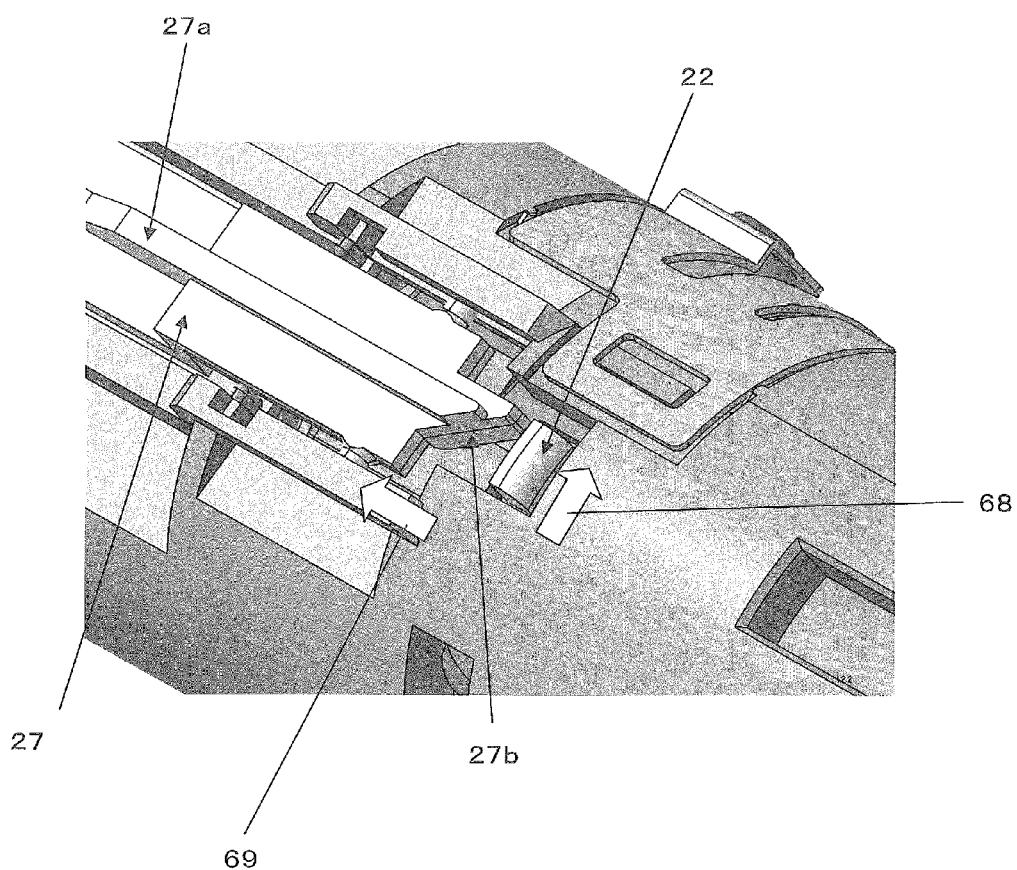
FIG. 9 is a detail view of the main components of the syringe holder.

Next, the engagement between the protrusions 22 of the detector rod 19 and the detecting lever 27 in a state in which the syringe holder 10 has been mounted inside the inner case 11 will be described through reference to FIGS. 8 and 9. FIG. 8 shows the state when the syringe holder 10 has been inserted into the inner case 11. FIG. 9 is a detail view of the area around the detecting lever 27 (the area C encircled by the dashed line in FIG. 8). After being inserted into the inner case 11, the syringe holder 10 is turned clockwise (to the right; the direction of the arrow 68 in FIG. 9). This clockwise turning causes the protrusions 22 of the detector rod 19 of the syringe holder 10 to protrude through the openings to the outside of the inner case 11, and these protruding portions are turned in the direction of the arrow 68 as discussed above. Consequently, the detecting lever 27 moves to the rear (the direction of the arrow 69 shown in FIG. 9).

That is, an inclined face 27b is formed on the front end side (syringe holder mounting opening side) of the detecting lever 27 as shown in FIG. 9. When this inclined face 27b is pushed by a protrusion 22 of the detector rod 19, the rear end of the detecting lever 27 moves to the rear the direction of the arrow 69 in FIG. 9).

The rear end of the detecting lever 27 is biased forward (the opposite direction from that of the arrow 69) by a spring (not shown). When the detecting lever 27 moves rearward against this biasing, the detecting sensor 28 detects this retraction.

That is, a state in which the syringe holder 10 is mounted in the inner case 11 is a state in which the needle 16 is mounted to the needle mount 17 of the syringe holder 10, and the syringe holder 10 is properly mounted inside the inner case 11, or in other words, a state in which the proper stand-by state is ensured.

As shown in FIG. 9, the reinforcing plate 27a is provided to the outer surface on the front end side (the syringe holder mounting opening side) of the detecting lever 27.

The reinforcing plate 27a extends from the front end side of the detecting lever 27 to the rear end side, and in particular is designed so that the front end side will not warp in the outer peripheral direction of the inner case 11.

That is, the protrusions 22 of the detector rod 19 project only slightly from the openings 23 (see FIG. 7). Therefore, it is extremely important for the front end side of the detecting lever 27 not to warp in the outer peripheral direction of the inner case 11 so that the protrusions 22 will contact the detecting lever 27 even with just this slight amount of projection, and will move the detecting lever 27 to the rearward side. Thus, the above-mentioned operation is ensured by providing the reinforcing plate 27a.

Also, because this reinforcing plate 27a is provided to the outer surface side of the flat detecting lever 27, even if the detecting lever 27 should stretch due to elevated temperature, the outer surface side of the reinforcing plate 27a will stretch more, so the distal end side of the detecting lever 27 will gently curve in the direction of the protrusions 22 of the detector rod 19. Consequently, the protrusions 22 of the detector rod 19 will contact the detecting lever 27 and properly move it to the rearward side.

Of course, there is the risk that the opposite could occur if the temperature should drop. However, the environment in which the pharmaceutical injection device 100 of this embodiment is used is assumed to be one with an ordinary room temperature. Therefore, when the main body case 1 is held in the user's hand during use, the temperature usually rises slightly under the body heat thereof, so it can be assumed that distortion of the detecting lever 27 caused by a drop in temperature will essentially not occur.

The mounting of the syringe holder 10 to the inner case 11 as discussed above is carried out as follows, as shown in FIGS. 3 to 7. First, the pharmaceutical syringe 50 is inserted into the syringe holder 10 from the piston insertion opening 15 side. After this, the needle 16 is mounted to the needle mount 17. At this point the needle 16 moves in the direction of the arrow 64 shown in FIG. 4 and engages with the detector rod 19, which pushes the detecting lever 27 in the direction of the arrow 64. In this state, as shown in FIG. 2, the syringe holder 10 is inserted in the direction of the arrow 61 into the syringe holder mounting opening 12 of the inner case 11. The syringe holder 10 is inserted into the inner case 11 and then turned clockwise (to the right; the direction of the arrow 68 in FIG. 9). This clockwise turning causes the protrusions 22 of the detector rod 19 of the syringe holder 10 to protrude through the openings to the outside of the inner case 11, and these protruding portions are turned in the direction of the arrow 68 in FIG. 9. Consequently, the detecting lever 27 of the inner case 11 moves to the rear (the direction of the arrow 69 shown in FIG. 9).

In the mounting of the syringe holder 10 and the inner case 11, the cap 7 shown in FIG. 1 is removed from the front end side of the main body case 1.

1.1.4. Motor 40

Next, the motor 40 shown in FIG. 11 will be described. FIG. 11 shows the motor 40 that is installed in the interior of the main body case 1. The motor 40 is made up of two main motors or the like, such as a slide motor 32 (an example of a movable member driver) and a geared motor 34 (an example of a piston driver). The slide motor 32 is an example of a needle insertion and withdrawal drive means. The geared motor 34 is an example of a piston drive means used when performing air venting, pharmaceutical injection, or the like.

In FIG. 11, a joint 36 engages with a member that links to the piston 14 (see FIG. 12) inside the inner case 11, and thereby holds the piston 14. Consequently, the inner case 11 and a slide case 37 move in a state in which the pharmaceutical syringe 50 has been mounted, in conjunction with the drive of the slide motor 32, and this inserts and withdraws the needle. The motor 40 is further provided with an encoder 35 that detects the rotational position, etc., of the geared motor 34, and a slide screw 33 at the protruding portion of the slide case 37 that covers the joint 36. The slide screw 33 is linked to the slide motor 32, and the slide screw 33 moves in the left and right direction in FIG. 11 in conjunction with the rotation of the slide motor 32. Consequently, the inner case 11 that is linked to the geared motor 34 and the joint 36 is moved in the left and right direction in FIG. 11, and the needle is inserted or withdrawn. The geared motor 34 rotates after the movement of the slide motor 32 (that is, after the needle has been inserted or withdrawn), and the members linked to the piston 14 are rotated, causing the piston 14 to slide. Consequently, if the needle has already been inserted, the drug inside the pharmaceutical syringe 50 is injected through the needle 16 into the body.

Figure 12:
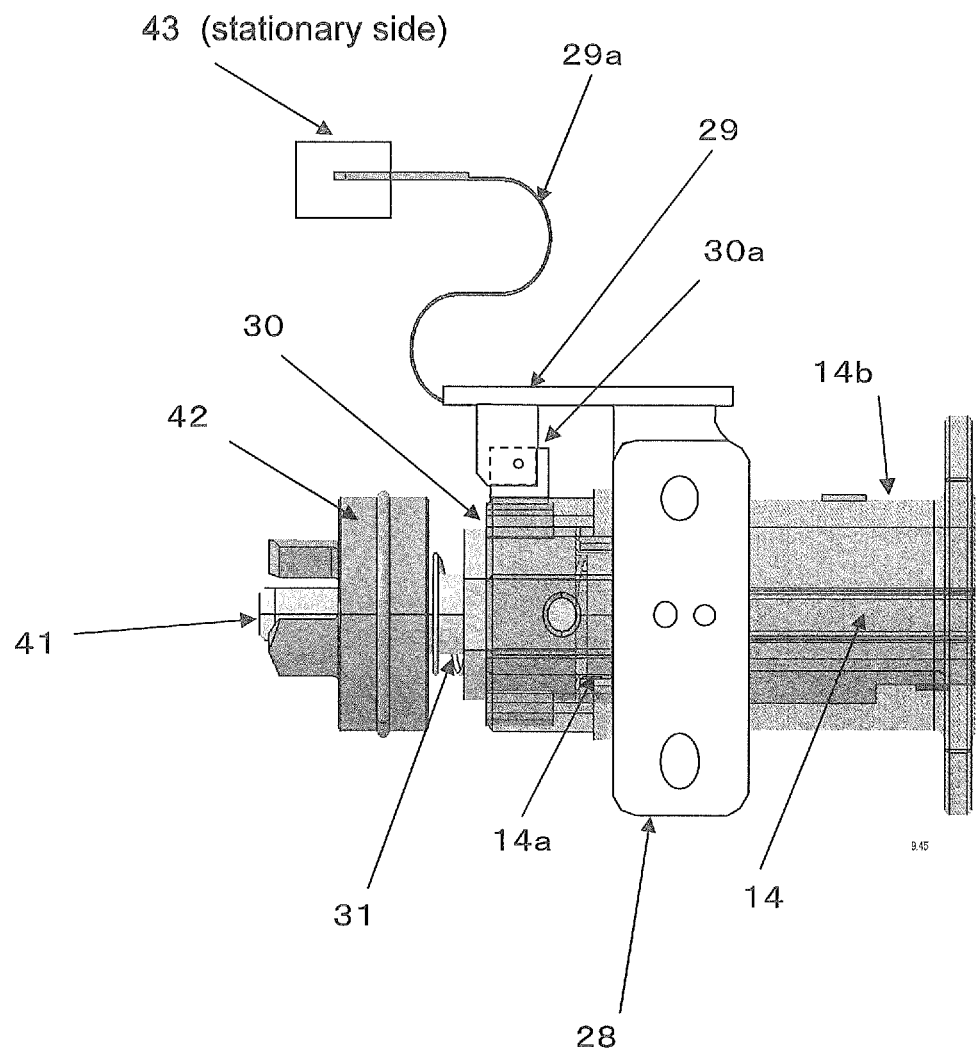
FIG. 12 is a diagram of the detector of the pharmaceutical injection device, and the surrounding area.

The amount of movement of the piston 14 is monitored by the encoder 35. As shown in FIG. 12, for example, the linking members between the piston 14 and the joint 36 are a coupling 42, a coupling prong 42a, etc. The rotational motion of the geared motor 34 is converted into linear motion by these linking members, and air venting and pharmaceutical injection are performed.

In the above-mentioned air venting, the home position of the piston 14 (discussed below) is confirmed by the detecting sensor 29 (an example of a second detector) shown in FIGS. 12 to 14. For this detection, a piston protrusion 14a is provided to the rear end of the piston 14. A position lever 30 is pushed to the rearward side (to the left in FIG. 12) by the piston protrusion 14a against a spring 31. The home position of the piston 14 is confirmed at this point from whether or not the light of the detecting sensor 29 is blocked by a blocking plate 30a of the position lever 30.

Here, the push shaft 41 shown in FIG. 12 is press-fitted to the coupling 42, and the distal end portion thereof is engaged with the piston 14. Consequently, the rotational motion of the geared motor 34 is reliably transmitted as linear motion to the piston 14.

1.1.5 Detecting Sensor

Figure 10:
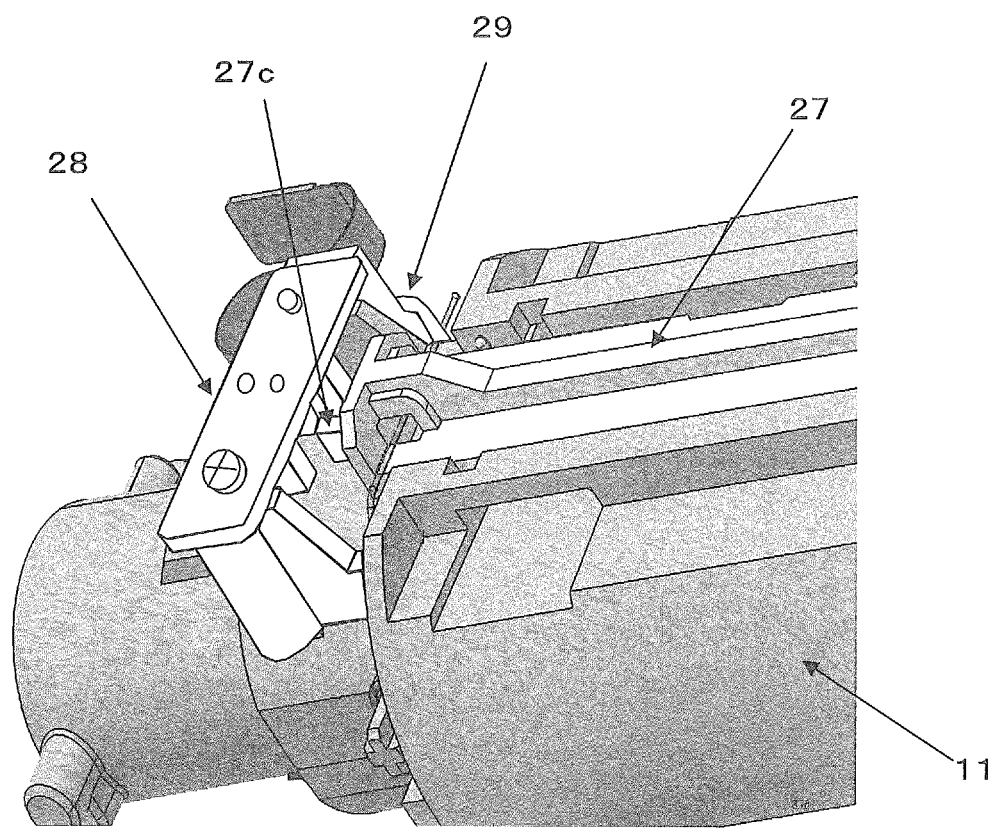
FIG. 10 is a detail view of other main components of the syringe holder.

FIG. 10 is a detail view of the main components of the detecting sensor 28 and its surroundings. The detecting sensor 28 in this embodiment comprises a photosensor that determines whether or not light has been blocked.

In FIG. 10, the detecting sensor 28 utilizes the detecting lever 27 provided to the inner case 11 to detect a mounted state when the syringe holder 10 to which the pharmaceutical syringe 50 and the needle 16 have been mounted has itself been mounted to the inner case 11, as discussed above. More precisely, the mount state is detected in consequence of the following. When the syringe holder 10 is mounted to the inner case 11, the detecting lever 27 moves to the rear end side of the main body case 1, and then a blocking plate 27c provided to the detecting lever 27 blocks optical elements of the detecting sensor 28. The optical elements of the detecting sensor 28 are made up of a light emitting element 28b and a light receiving element 28c (FIG. 13), and optical detection is performed when the blocking plate 27c moves in between the light emitting element 28b and the light receiving element 28c.

The detecting sensor 29 detects that the piston 14 is at its home position, that is, its initial position. The initial position of the piston 14 here is the initial position of the piston 14 with respect to the inner case 11 prior to pharmaceutical injection. More precisely, as shown in FIGS. 12 to 14, the optical elements of the detecting sensor 29 (a light emitting element 29b and a light receiving element 29c) and the position lever blocking plate 30a that blocks these off (see FIGS. 12 and 14) are provided, and when the piston 14 comes back to its home position, the piston protrusion 14a provided to the rear end of the piston 14 moves to the home position side and contacts the position lever 30. Further, when the piston 14 moves to the home position side, the spring 31 contracts, the position lever 30 also moves to its home position, and the blocking plate 30a provided to the position lever 30 blocks off the above-mentioned optical elements (29b and 29c). This is how it is detected that the piston 14 is located at its home position.

Figure 13:
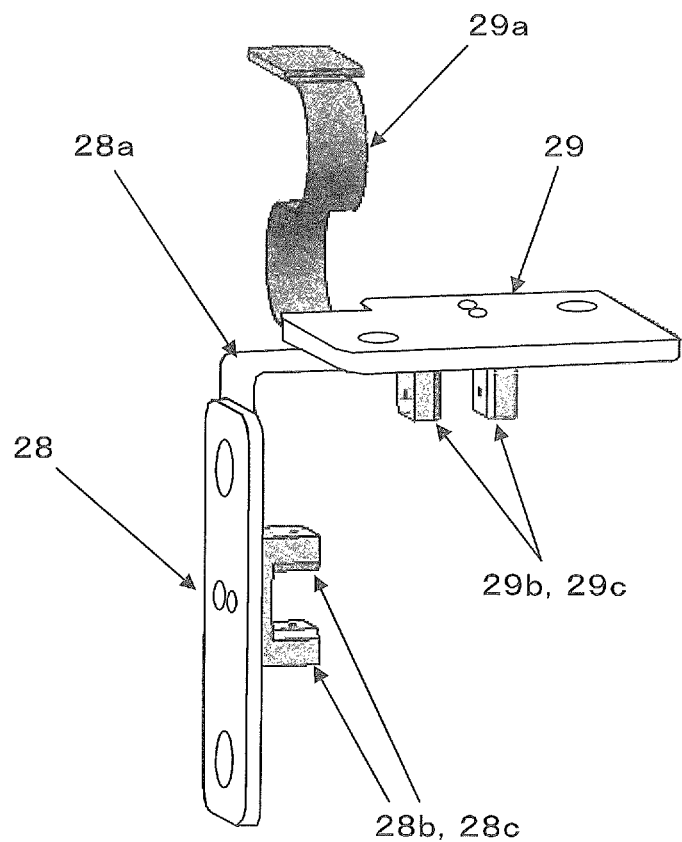
FIG. 13 is a detail view of the detector.
Figure 14:
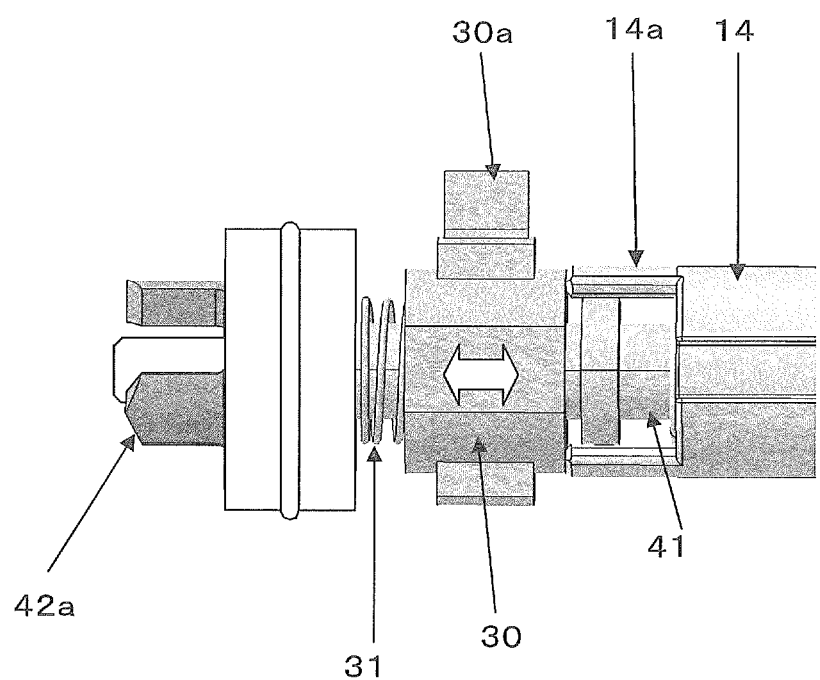
FIG. 14 is a diagram of the linking between the motor and piston of the pharmaceutical injection device.

FIG. 13 shows the above-mentioned detecting sensor 28 and detecting sensor 29. The detecting sensor 28 and the detecting sensor 29 are disposed at an angular position of 90 degrees with respect to the center axis of the inner case 11. This angular position may instead be 180 degrees. As discussed above, the detecting sensor 28 has the light emitting element 28b and the light receiving element 28c, which are optical elements. The detecting sensor 29 has the light emitting element 29b and the light receiving element 29c, which are also optical elements. That is, the detecting sensors 28 and 29 perform optical detection. The detection signals optically detected by the detecting sensors 28 and 29 are sent via a flexible cable 29a to a connector 43 inside the main body case (stationary side), and inputted to a controller 103 on the inside. The detecting sensors 28 and 29 are provided to the end of the inner case 11, and move together with the inner case 11 when the needle is inserted or withdrawn. Using the flexible cable 29a allows the inner case 11 to freely insert and withdraw the needle.

The pharmaceutical syringe 50 held in the syringe holder 10 is held along with the syringe holder 10 in the inner case 11, and during the above-mentioned insertion or withdrawal operation there is no change in the positional relation between the syringe holder 10, the pharmaceutical syringe 50, the detecting sensor 28, and the detecting sensor 29. Thus, detection accuracy can be improved, the mounting state of the syringe holder 10 can be ascertained at all times, and safety can be enhanced by detecting any abnormalities in the mounting state during the use of the pharmaceutical injection device 100.

With this embodiment, the detecting sensor 28 detects the mounting only when both the syringe holder 10 and the needle 16 have been mounted. Thus, if either one has not been properly mounted, the detecting sensor 28 does not detecting mounting, it is determined that the pharmaceutical injection device is not yet ready, and it is impossible to proceed to the next operation, which improves safety.

1.2 Operation of Pharmaceutical Injection Device 100

With the pharmaceutical injection device 100 pertaining to this embodiment, first, in the state in FIG. 1, the power button 5 is pressed and the needle cap 18 is removed from the opening 9. In this state the opening 9 side is turned to face up, after which the air venting button 3 is pressed. This starts the air venting operation.

When confirmation of the mounting of the syringe holder 10 and the needle 16 by the detecting sensor 28 is finished, the slide motor 32 moves the entire inner case 11 and the slide case 37 to the front end side of the main body case 1 via the slide screw 33 (see FIG. 11). Consequently, the distal end of the needle 16 sticks out forward from the opening 9 in the cap 7, and the needle 16 punctures the skin.

After this, the piston 14 is moved to the forward side by the geared motor 34, and the front end of the piston 14 presses on a pressing plate (not shown) at the rear end of the pharmaceutical syringe 50 provided inside the syringe holder 10. Consequently, part of the drug in the pharmaceutical syringe 50 flows out from the distal end of the needle 16, and as a result, the interior of the pharmaceutical syringe 50 and the needle 16 are vented.

After this, the end button 4 is pressed to reverse the rotation of the slide motor 32 so as to reach a specific value, and return to the initial state shown in FIG. 1. The system may also be designed so as to return to the state in FIG. 1 automatically, without pressing the end button.

When the above-mentioned air venting operation is finished, the flow then moves to a pharmaceutical injection operation. The cap 7 of the pharmaceutical injection device 100 is brought into contact with the injection site on the body (such as the skin of a person), and if the pharmaceutical injection button 6 is pressed in this state, the slide motor 32 moves the entire inner case 11 via the slide screw 33 to the front end side of the main body case 1. Consequently, the distal end of the needle 16 sticks out forward beyond the opening 9 in the cap 7, and is inserted into the body.

After this, if the piston 14 is moved to the forward side by the geared motor 34, the front end of the piston 14 presses on a pressing plate (not shown) at the rear end of the pharmaceutical syringe 50 inside the syringe holder 10. Consequently, part of the drug inside the pharmaceutical syringe 50 is injected in the specified amount from the distal end of the needle 16 into the body.

1.3 Control Circuit of Pharmaceutical Injection Device 100

Figure 15:
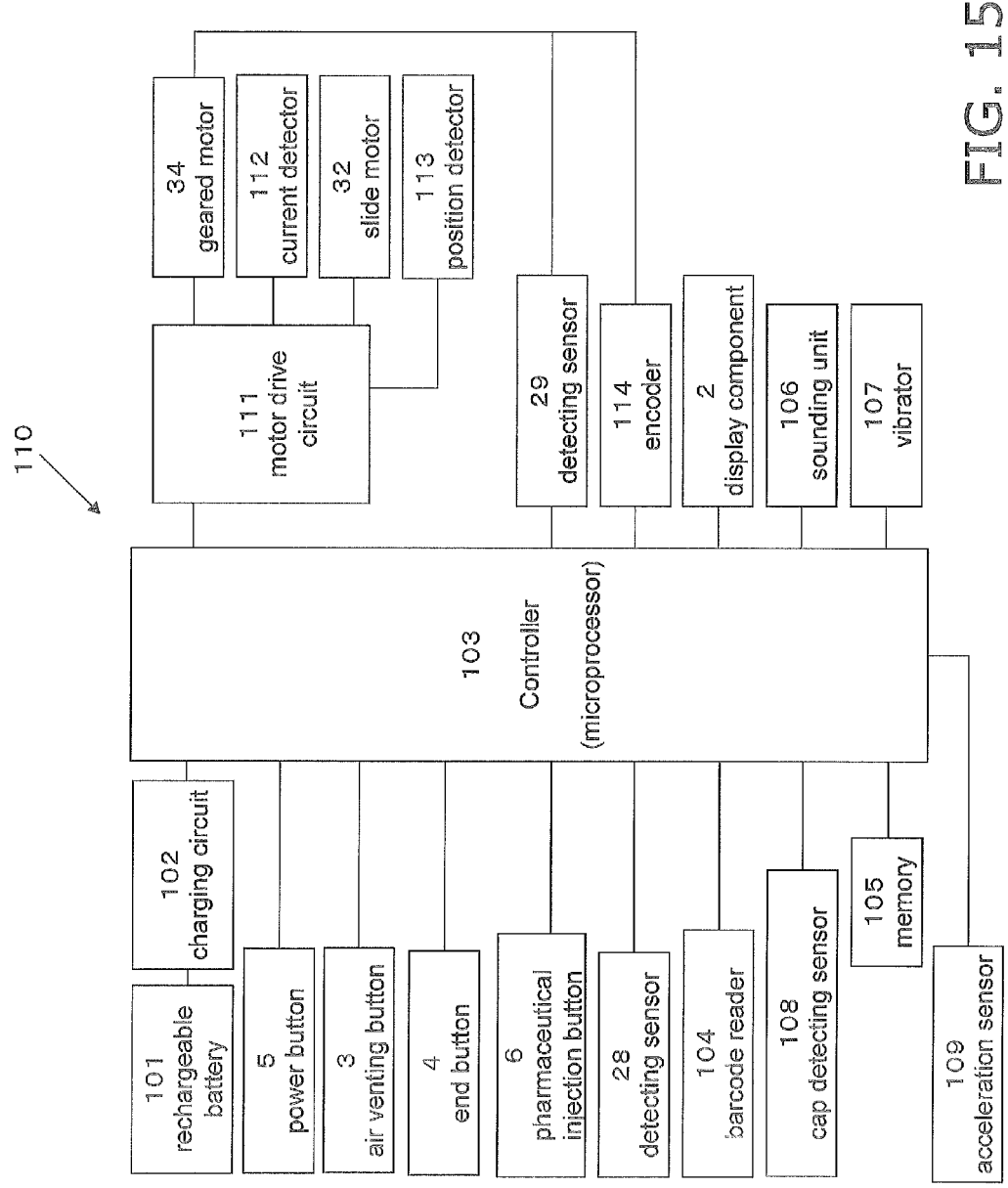
FIG. 15 is a diagram of the configuration of a control circuit in the pharmaceutical injection device.

FIG. 15 is a block diagram of the control circuit of the pharmaceutical injection device 100 pertaining to this embodiment, and the surrounding components. In FIG. 15, a controller 103 is connected to a charging circuit 102 that is used to charge a rechargeable battery 101. The controller 103 is also connected to various input/output components, such as the power button 5, the air venting button 3, the end button 4, the pharmaceutical injection button 6, the display component 2 (an example of a notification component), a sounding unit 106 (an example of a notification component), a vibrator 107 (an example of a notification component) having a vibration function, and a barcode reader 104 for ID management, and is further connected to a motor drive circuit 111. The motor drive circuit 111 inputs signals from a current detector 112 that monitors motor current, a position detector 113 that detects the position of the piston 14, and an encoder 114 that monitors the rotation of the motor. The motor drive circuit 111 controls the drive of the geared motor 34 (used to drive the piston 14) and the slide motor 32 (used for inserting and withdrawing the needle).

The controller 103 is also connected to the detecting sensor 28 (which detects the mounting state of the needle 16 and/or the syringe holder 10 to the inner case 11), the detecting sensor 29 (for detecting the home position of the piston 14), and a cap detecting sensor 108 that detects the mounting of the cap 7. The controller 103 is able at all times to detect the mounting state of the syringe holder 10 and/or the needle 16 according to signals from the detecting sensor 28.

The controller 103 has a microprocessor, computes or refers to data stored in a memory 105, and records the amount of drug injected in the memory 105.

The pharmaceutical injection device 100 is also provided with an acceleration sensor 109 that detects the inclination of the main body case 1. This acceleration sensor 109 is a three-dimensional acceleration sensor, and detects inclination information three-dimensionally.

1.4 Processing by Pharmaceutical Injection Device 100

Figure 16:
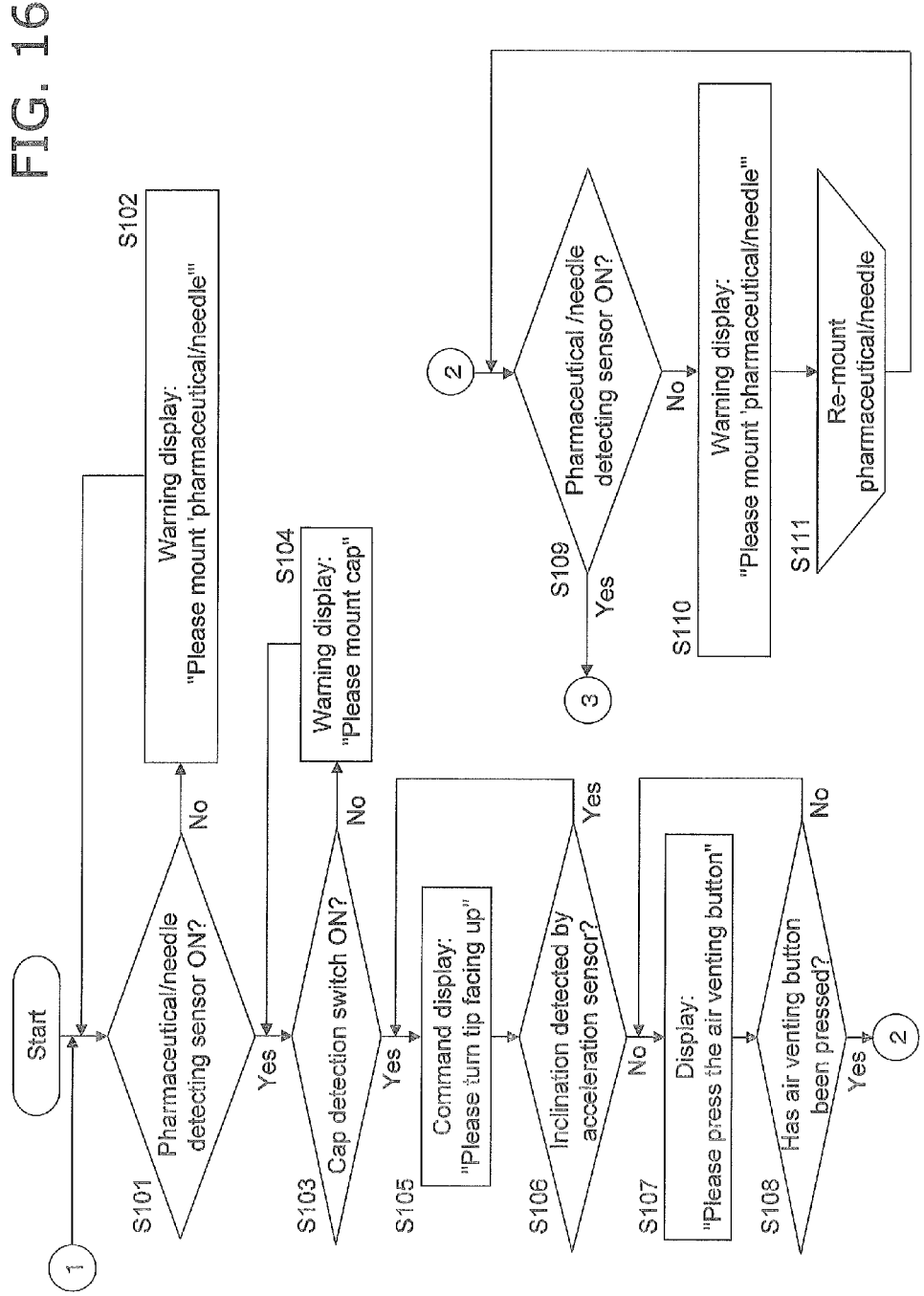
FIG. 16 is a flowchart of the processing performed by the pharmaceutical injection device.
Figure 17:
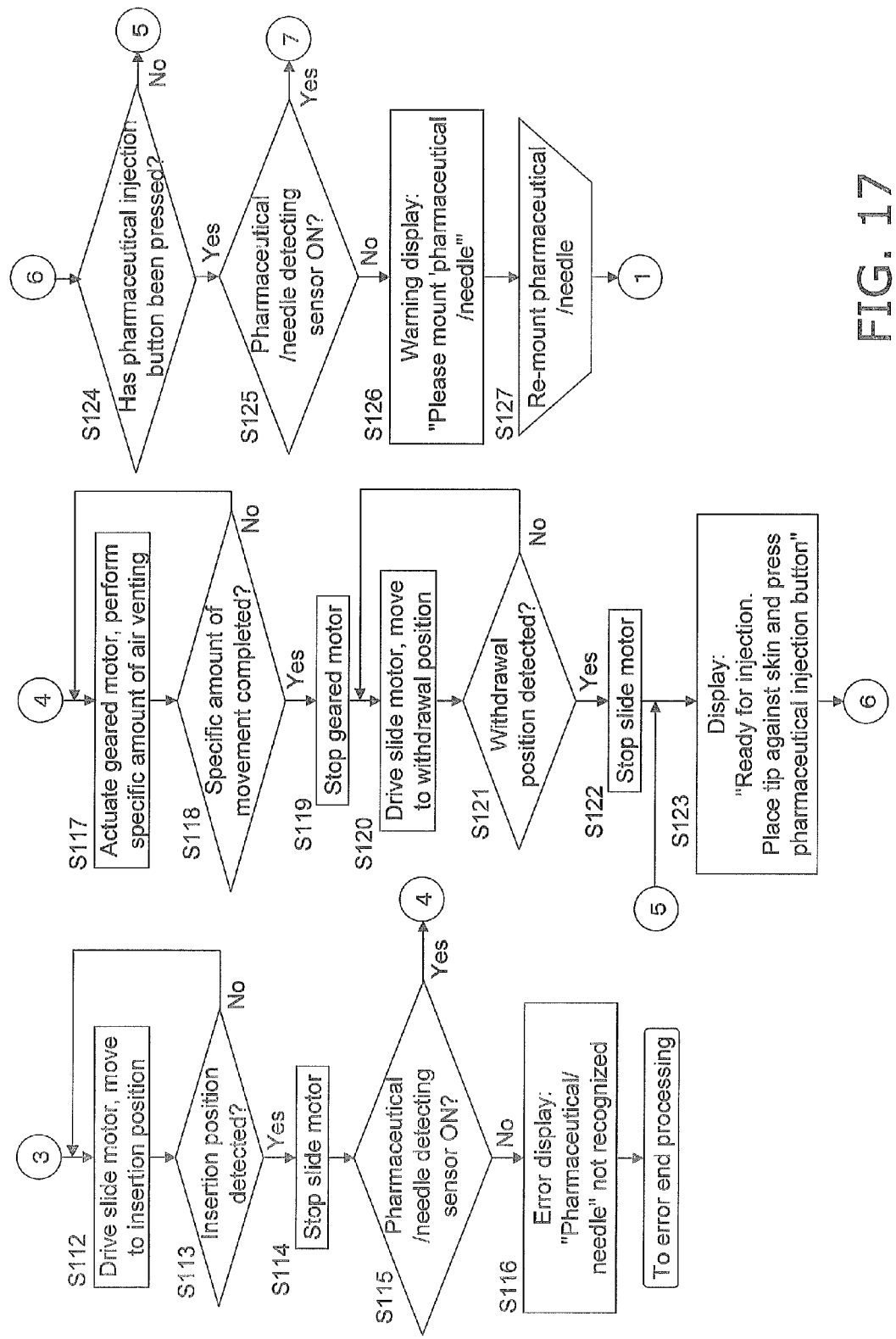
FIG. 17 is a flowchart of the processing performed by the pharmaceutical injection device.
Figure 18:
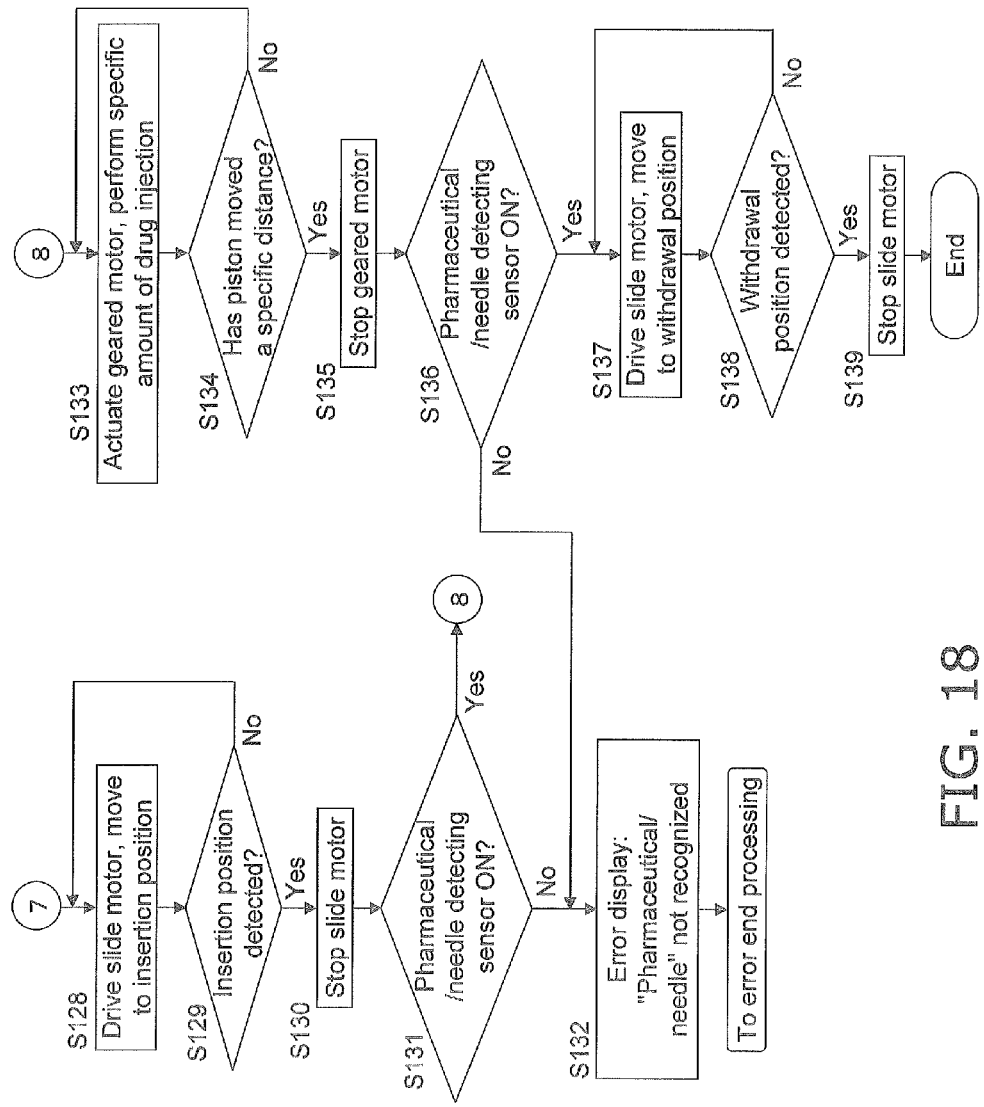
FIG. 18 is a flowchart of the processing performed by the pharmaceutical injection device.

FIGS. 16 to 18 are flowcharts of the operation in this embodiment. In a state in which the pharmaceutical syringe 50 has been installed and the needle 16 has been mounted in the syringe holder 10, and the syringe holder 10 has been mounted to the inner case 11 of the main body case 1, the user presses the power button 5 to turn on the pharmaceutical injection device 100.

1.4.1 Air Venting

Step S101: When the power button 5 is pressed, the mounting state of the syringe holder 10 and/or the needle 16 (in the following description and the drawings, this will sometimes be referred to as the pharmaceutical/needle mounting state) is detected by the detecting sensor 28. If the pharmaceutical/needle mounting state is OK (if the detecting sensor 28 is on), the flow proceeds to step S103, but if the mounting is incorrect (if the detecting sensor 28 is off), the flow proceeds to step S102.

Step S102: A message recommending the mounting of the "pharmaceutical/needle" is displayed on the display component 2 of the main body case 1, and the system awaits the mounting of the syringe holder 10 and/or the needle 16 (returns to step S101).

Step S103: The mounting state of the cap 7 is detected by the cap detecting sensor 108. If the cap detecting sensor 108 is in its on state (if the cap has been mounted), the flow proceeds to step S105, but if it is in its off state (if the cap has not been mounted), the flow proceeds to step S104.

Step S104: A message recommending the mounting of the "cap" is displayed on the display component 2 of the main body case 1, and the system awaits the mounting of the cap 7 (returns to step S103).

Step S105: In a state in which the above preparations have been made, the flow proceeds to "air venting." A message is displayed on the display component 2 recommending the user to turn the distal end side of the main body case 1 (the side on which the cap 7 is mounted) upward.

Step S106: The inclination of the main body case 1 is detected by the acceleration sensor 109. If the acceleration sensor 109 detects that the angle between the ground and the vertical direction is within a specific range, the flow proceeds to step S107. Here, the distal end side of the main body case 1 only needs to be pointing slightly upward in order to perform air venting, but preferably the specific angle is defined to be a range of −45 to +45 degrees between the ground and the vertical direction. A range of −30 to +30 degrees is even more effective.

Step S107: In a state in which the distal end of the main body case 1 is facing upward, a message recommending the user to press the "air venting button" is displayed on the display component 2, and the system waits for the user to press the air venting button 3.

Step S108: When the pressing of the "air venting button" is detected, the flow proceeds to step S109.

Step S109: The mounting state of the syringe holder 10 and/or the needle 16 is detected again by the detecting sensor 28. If there is no problem with the mounting, the flow proceeds to step S112 (FIG. 17). If the mounting is incorrect, the flow proceeds to step S110.

Step S110: A message recommending the user to mount the syringe holder 10 and/or the needle 16 is displayed on the display component 2.

Step S111: The syringe holder 10 and the needle 16 are mounted by the user, and the mounting state is again detected (return to step S109).

Step S112: After the preparations for "air venting" have been finished by the processing shown in FIG. 16, the slide motor 32 is driven by the motor drive circuit 111 to move the syringe holder 10 and the inner case 11 to the insertion position as shown in FIG. 17.

Step S113: A signal from the position detector 113 is inputted via the motor drive circuit 111 to the controller 103 (see FIG. 15) to detect whether or not the syringe holder 10 and the inner case 11 have moved to the insertion position.

Step S114: Once the movement to the insertion position is complete, the slide motor 32 is stopped.

Step S115: The mounting state of the syringe holder 10 and/or the needle 16 is detected again by the detecting sensor 28. If the mounting is OK, the flow proceeds to step S117. If the mounting is incorrect, the flow proceeds to step S116.

Step S116: An error display indicating a problem is shown on the display component 2, the operation is halted, and error processing forcibly ends the flow.

Step S117: The geared motor 34 is driven by the motor drive circuit 111, the piston 14 is moved a specific amount, and the front end of the piston 14 presses on a pressing plate (not shown) at the rear end of the pharmaceutical syringe 50 provided inside the syringe holder 10. Consequently, part of the drug inside the pharmaceutical syringe 50 flows out from the distal end of the needle 16, and air venting is thus performed.

Step S118: The end of movement of the piston 14 by a specific amount is detected. At this point, the amount of movement of the geared motor 34 is detected by the encoder 114, etc., connected to the controller 103.

Step S119: The geared motor 34 is stopped, thus ending the air venting operation.

Step S120: The slide motor 32 is driven by the motor drive circuit 111, and the syringe holder 10 and the inner case 11 are moved to the withdrawal position.

Step S121: Movement to the withdrawal position is detected. A signal from the position detector 113 is inputted via the motor drive circuit 111 to the controller 103 (see FIG. 15) to detect whether or not the syringe holder 10 and the inner case 11 have moved (returned) to the withdrawal position.

Step S122: The slide motor 32 is stopped. At this point preparations for pharmaceutical injection are complete.

1.4.2 Needle Insertion

Step S123: A message of "drug can be injected" is shown, and a message recommending the user to place the cap mounting side of the pharmaceutical injection device against the skin and to press the "injection button 6" is displayed on the display component 2.

Step S124: The pressing of the "injection button 6" is detected by the controller 103.

Step S125: If the pharmaceutical injection button 6 is pressed, the mounting of the syringe holder 10 and/or the needle 16 is again detected. If the mounting is OK, the flow proceeds to the insertion operation of step S128 (FIG. 18). If the mounting is incorrect, the flow proceeds to step S126.

Step S126: A warning display is given to indicate that the syringe holder 10 and/or the needle 16 should be mounted.

Step S127: When the pharmaceutical/needle mounting is performed by the user, the flow returns to step S101.

Step S128: As shown in FIG. 18, the slide motor 32 is driven by the motor drive circuit 111, and the syringe holder 10 and the inner case 11 are moved to the insertion position.

Step S129: A signal from the position detector 113 is inputted via the motor drive circuit 111 to the controller 103 (see FIG. 15) to detect whether or not the syringe holder 10 and the inner case 11 have reached the insertion position.

Step S130: After detection, the slide motor 32 is stopped. At this point, since the cap 7 is in contact with the skin, the needle 16 inside the cylindrical cap 7 sticks out from the distal end and punctures the skin.

1.4.3 Pharmaceutical Injection Operation

Step S131: The mounting state of the syringe holder 10 and/or the needle 16 is detected. If the mounting is OK, the flow proceeds to step S133. If the mounting is incorrect, the flow proceeds to step S132.

Step S132: An error display is shown on the display component 2, the operation is halted, and then error processing forcibly ends the flow.

Step S133: The geared motor 34 is driven to move the piston 14. This begins the injection of the drug inside the pharmaceutical syringe 50.

Step S134: The encoder 114 detects whether or not the piston 14 has moved a specific distance corresponding to a specific amount of drug. When movement by the specified distance is detected, the flow proceeds to step S135.

Step S135: The geared motor 34 is stopped, as is the movement of the piston 14. As a result, the specified amount of drug is injected into the body.

Step S136: The mounting state of the syringe holder 10 and/or the needle 16 is detected. If the mounting is OK, the flow proceeds to step S137. If the mounting is incorrect, the flow returns to step S132, an error display is shown on the display component 2, and the operation is halted by error processing.

Step S137: The syringe holder 10 and the inner case 11 are moved to the withdrawal position by the slide motor 32. That is, the needle 16 is withdrawn from the skin.

Step S138: A signal from the position detector 113 is inputted via the motor drive circuit 111 to the controller 103 (see FIG. 15) to detect that the syringe holder 10 and the inner case 11 have reached the withdrawal position.

Step S139: When movement to the withdrawal position is detected, the slide motor 32 is stopped and the pharmaceutical injection operation is ended.

As discussed above, in the steps involved in pharmaceutical injection, that the syringe holder 10 and/or the needle 16 is not mounted or is incorrectly mounted can be discovered earlier by constantly monitoring the mounting state of these two. Consequently, an abnormal state of the device can be discovered earlier and the device can be stopped before moving on to the next operation, and since these measures can be taken rapidly, the user can earlier confirm an abnormal state or incorrect mounting of the device, allowing the device to be used properly and safely.

1.5 Features of Embodiment 1

The pharmaceutical injection device 100 pertaining to the above-mentioned Embodiment 1 comprises the inner case 11 that can move with respect to the main body case 1, the syringe holder 10 to which is mounted the needle 16 mounted to the inner case 11, the detector rod 19 that is mounted to the inner case 11 and is used to detect mounting of the needle 16, and the detecting sensor 28 provided to the inner case 11, and therefore, after the syringe holder 10 has been mounted to the inner case 11, the positional relation between the needle 16, the detector rod 19, the inner case 11, and the detecting sensor 28 is fixed, so the mounting state of the needle/pharmaceutical can be detected more accurately, and safety can be improved.

Consequently, the mounting state of the syringe holder 10 and the needle 16 can be monitored constantly, and even if a problem with this mounting state should occur during operation, this can be dealt with by automatically halting the operation of the device, displaying a warning, etc.

Also, deterioration over the years caused by movement of the inner case 11 can be prevented from adversely affecting the accuracy of detection of the mounting state of the syringe holder 10 and the needle 16.

1.6 Modification Example of Embodiment 1

Figure 19:
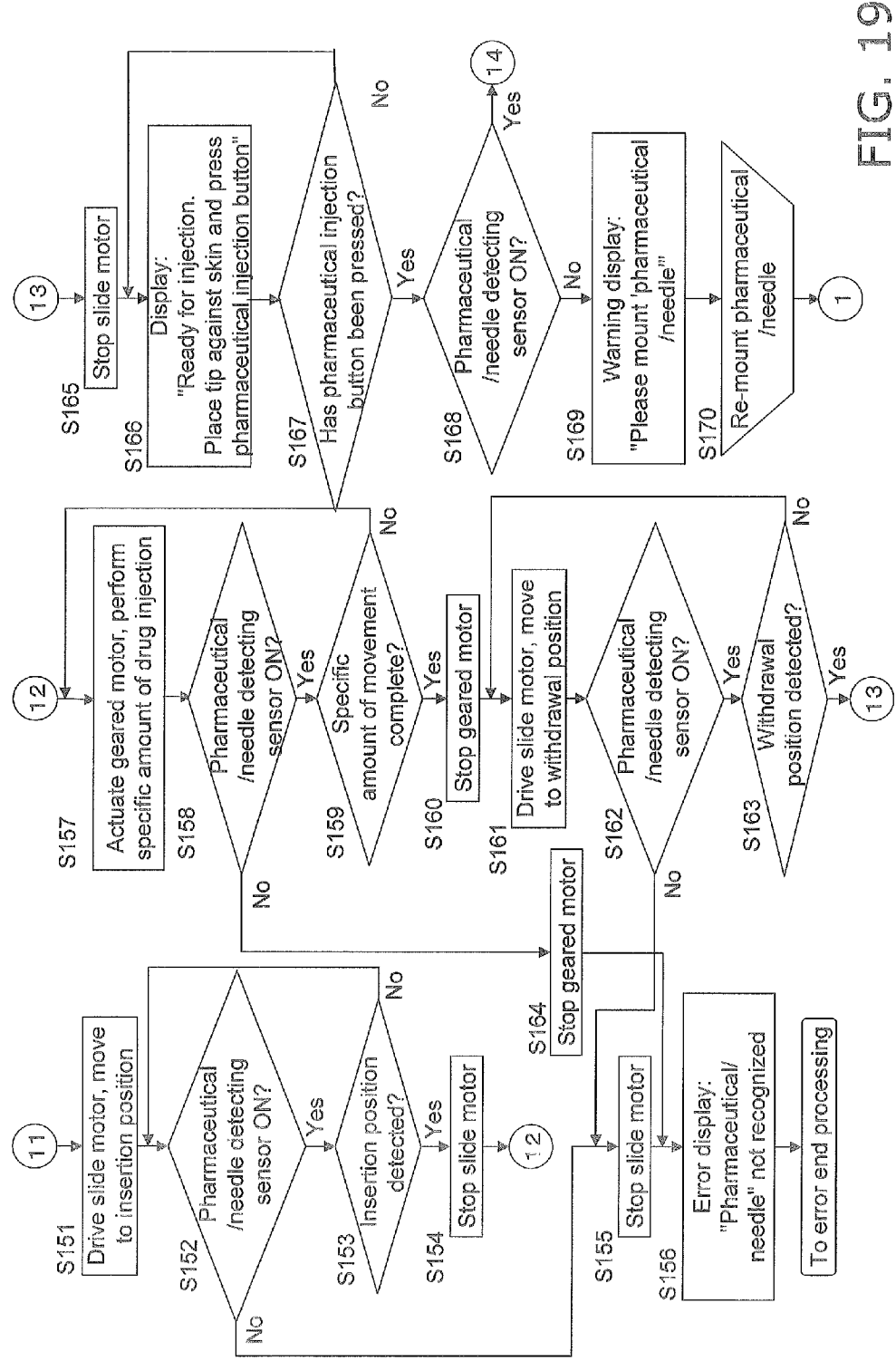
FIG. 19 is a flowchart of the processing performed by the pharmaceutical injection device pertaining to a modification example of Embodiment 1.
Figure 20:
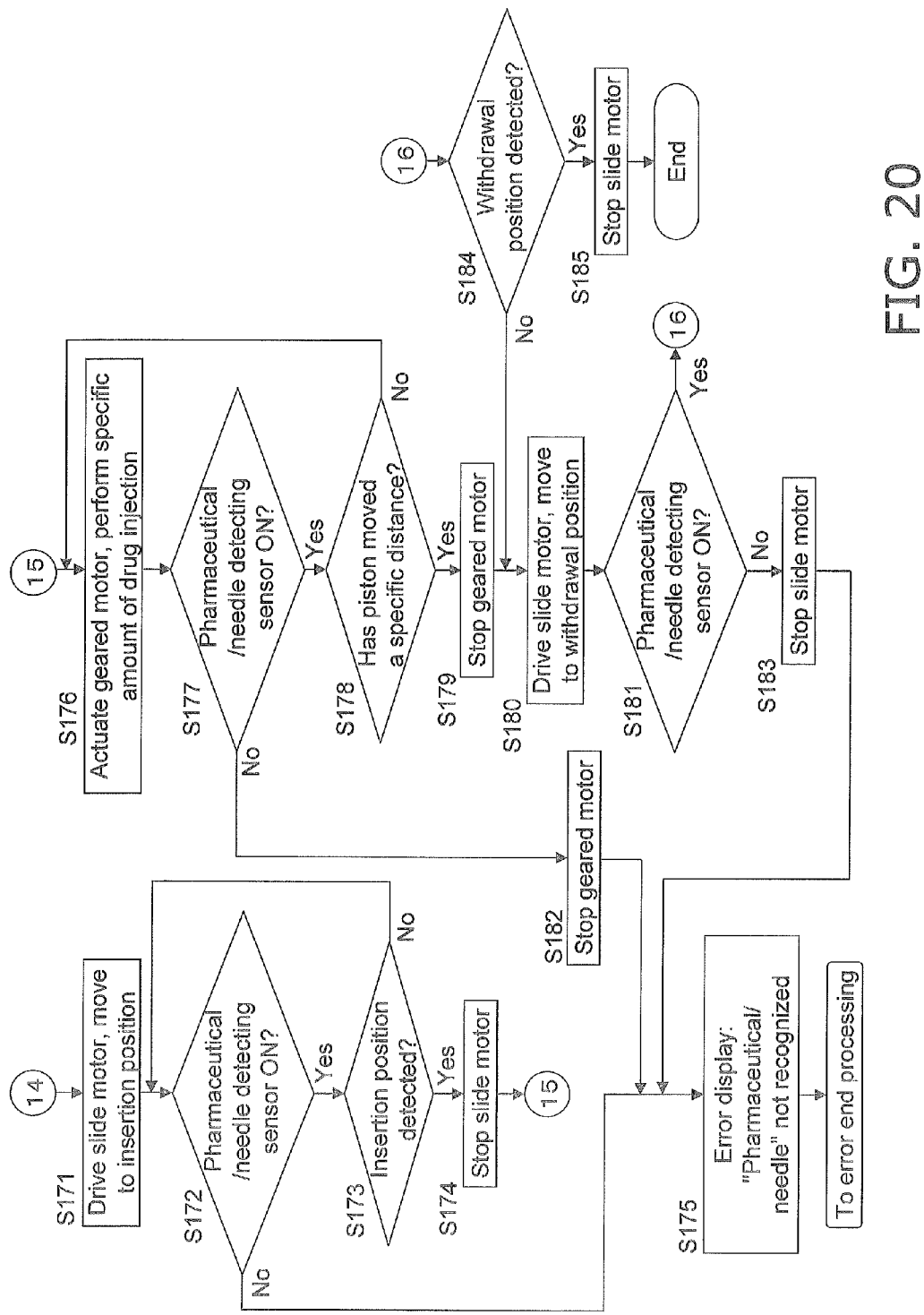
FIG. 20 is a flowchart of the processing performed by the pharmaceutical injection device pertaining to the modification example.

Next, FIGS. 19 and 20 show the processing of the pharmaceutical injection device 100 pertaining to a modification example of this embodiment. The difference here is a change in the timing at which the detecting sensor 28 detects the mounting state of the syringe holder 10 and/or the needle 16 during operation corresponding to steps S112 to S139 (from air venting to the end of the pharmaceutical injection operation) shown in FIGS. 17 and 18 as discussed above.

In FIGS. 19 and 20, confirmation of the detection of the detecting sensor 28 is also performed during the operation of the motor 40. Therefore, even if something unexpected should happen during the operation of the motor 40, resulting in an incorrect mounting state of the syringe holder 10 and/or the needle 16, this will be detected automatically and the running motor can be put in emergency shut-down, which contributes to better safety. This will be described in detail below through reference to FIGS. 19 and 20.

1.6.1 Air Venting

Step S151: First, preparations are performed in which the syringe holder 10 and/or the needle 16 is mounted to the inner case 11, after which the cap 7 is mounted, and in a state in which the air venting button 3 has been pressed, the slide motor 32 is driven and begins moving the syringe holder 10 and the inner case 11 to the insertion position.

Step S152: The mounting state of the syringe holder 10 and/or the needle 16 is detected. If the mounting is incorrect during the running of the slide motor 32 here, the flow proceeds to step S155.

Step S153: If there is no problem with the mounting of the syringe holder 10 and/or the needle 16, etc., a signal from the position detector 113 is inputted via the motor drive circuit 111 to the controller 103 to detect whether or not the syringe holder 10 and the inner case 11 have moved to the insertion position. If the movement to the insertion position has been correctly completely, the flow proceeds to step S154.

Step S154: Once the movement to the insertion position is complete, the slide motor 32 is stopped.

Step S155: If there is a problem with mounting in step S152, an error is determined to exist, and the slide motor 32 is stopped.

Step S156: An error message is displayed on the display component 2, operation is halted, and error processing forcibly ends the flow. At this point a warning sound may be emitted from the sounding unit 106, or the vibrator 107 may be actuated to provide notification by vibration.

Step S157: The geared motor 34 used for moving the piston 14 is driven by the motor drive circuit 111, which moves the piston 14 and commences the air venting operation.

Step S158: The mounting state of the syringe holder 10 and/or the needle 16 is also detected during the drive of the geared motor 34 in step S157. If incorrect mounting is detected during the drive of the geared motor 34, the flow proceeds to step S164.

Step S159: If there is no problem in the above-mentioned mounting, the encoder 114 detects the completion of a specific amount of movement of the piston 14 corresponding to a specific amount of air venting. The amount of movement of the geared motor 34 can be detected by the encoder 114 connected to the controller 103, for example.

Step S160: The geared motor 34 is stopped. This ends the air venting operation.

Step S161: The slide motor 32 is driven to move the syringe holder 10 and the inner case 11 to the withdrawal position.

Step S162: The mounting state of the syringe holder 10 and/or the needle 16 is also detected during the drive of the slide motor 32 in step S161. If incorrect mounting is detected, an error is determined to exist, the flow returns to step S155, the slide motor 32 is stopped (step S155), and an error message is displayed (step S156), after which the operation is halted (forcibly ended) by error processing.

Step S163: If there is no problem in the mounting of the syringe holder 10 and/or the needle 16, a signal from the position detector 113 is inputted via the motor drive circuit 111 to the controller 103 to detect that the syringe holder 10 and/or the needle 16 has moved correctly to the withdrawal position.

Step S164: If incorrect mounting is detected in step S158, an error is determined to exist, the geared motor 34 is stopped, and an error message is displayed (step S156), after which the operation is halted and the flow is forcibly ended by error processing.

Step S165: If it is detected that the syringe holder 10 and the inner case 11 have correctly moved to the withdrawal position, the slide motor 32 is stopped.

Step S166: Next, messages of "injection preparation complete," "place tip against skin," and "press pharmaceutical injection button" are displayed on the display component 2, and the flow proceeds to the pharmaceutical injection operation.

1.6.2 Insertion Operation

Step S167: The controller 103 detects that the user has pressed the pharmaceutical injection button 6.

Step S168: The mounting of the syringe holder 10 and/or the needle 16 is confirmed, and if the mounting is OK, the flow proceeds to step S171.

Step S169: If the mounting is incorrect, a warning message telling the user to mount the syringe holder 10 and/or the needle 16 is displayed.

Step S170: Once the pharmaceutical/needle has been mounted by the user, the flow returns to step S101.

Step S171: The slide motor 32 is driven and needle insertion is commenced.

Step S172: The mounting state of the syringe holder 10 and/or the needle 16 is also detected during the motor operation in step S171.

Step S173: A signal from the position detector 113 is inputted via the motor drive circuit 111 to the controller 103 to detect whether or not the syringe holder 10 and the inner case 11 have moved to the insertion position.

Step S174: After detection, the slide motor 32 is stopped and the flow proceeds to step S176. At this point, since the cap 7 is in contact with the skin, the needle 16 inside the cylindrical cap 7 sticks out from the distal end and punctures the skin.

Step S175: If it is detected that the mounting of the syringe holder 10 and/or the needle 16 is incorrect during the running of the motor in step S172, abnormality is determined, then the driving slide motor 32 is stopped, an error message is displayed on the display component 2, and the operation is halted, after which the flow is forcibly ended by error processing.

1.6.3 Pharmaceutical Injection Operation

Step S176: The geared motor 34 is driven to move the piston 14. This commences the injection of the drug contained in the pharmaceutical syringe 50.

Step S177: If incorrect mounting of the syringe holder 10 and/or the needle 16 is detected during the running of the motor in step S176, the flow proceeds to step S182.

Step S178: The encoder 114 detects whether or not the piston 14 has moved a specific distance corresponding to a specific amount of drug. When movement by the specified distance is detected, the flow proceeds to step S179. If it is not detected that this distance has been reached (that is, if the distance has not been reached), the flow returns to step S176.

Step S179: The geared motor 34 is stopped, which stops the movement of the piston 14. As a result, a specific amount of drug is injected into the body.

Step S180: The slide motor 32 is driven to move the syringe holder 10 and the inner case 11 to the withdrawal position. That is, the needle 16 is withdrawn from the skin.

Step S181: The mounting state of the syringe holder 10 and/or the needle 16 is also detected during the drive of the slide motor 32 in step S180. If incorrect mounting is detected, the flow proceeds to step S183.

Step S182: If incorrect mounting of the syringe holder 10 and/or the needle 16 is detected in step S177, an error is determined to exist, the driving motor 34 is stopped, and the operation is halted (forcibly ended) by error processing (step S175).

Step S183: If incorrect mounting of the syringe holder 10 and/or the needle 16 is detected in step S181, the driving slide motor 32 is stopped, an error message is displayed (step S175), and then the operation is halted (forcibly ended) by error processing.

Step S184: A signal from the position detector 113 is inputted via the motor drive circuit 111 to the controller 103 to detect that the syringe holder 10 and the inner case 11 have reached the withdrawal position.

Step S185: The slide motor 32 is stopped and the pharmaceutical injection operation is ended. This completes the withdrawal operation in which the needle 16 is withdrawn from the skin.

As discussed above, with the processing of the pharmaceutical injection device 100 in this modification example, even if something unexpected should happen during the operation of the motor 40, resulting in an incorrect mounting state of the syringe holder 10 and the needle 16, this will be detected automatically because of constant monitoring, and the running motor can be put in emergency shut-down, which contributes to better safety.

2. Embodiment 2

2.1 Configuration of Pharmaceutical Injection Device 200

The pharmaceutical injection device 200 pertaining to Embodiment 2 of the present invention will be described through reference to FIGS. 21 to 25. This embodiment differs from Embodiment 1 above in that a detector having an RF-ID (an example of a wireless tag) is provided to the inner case, making wireless communication with the device main body side possible. Those components that are the same as in Embodiment 1 will be numbered the same and will not be described again.

Figure 21:
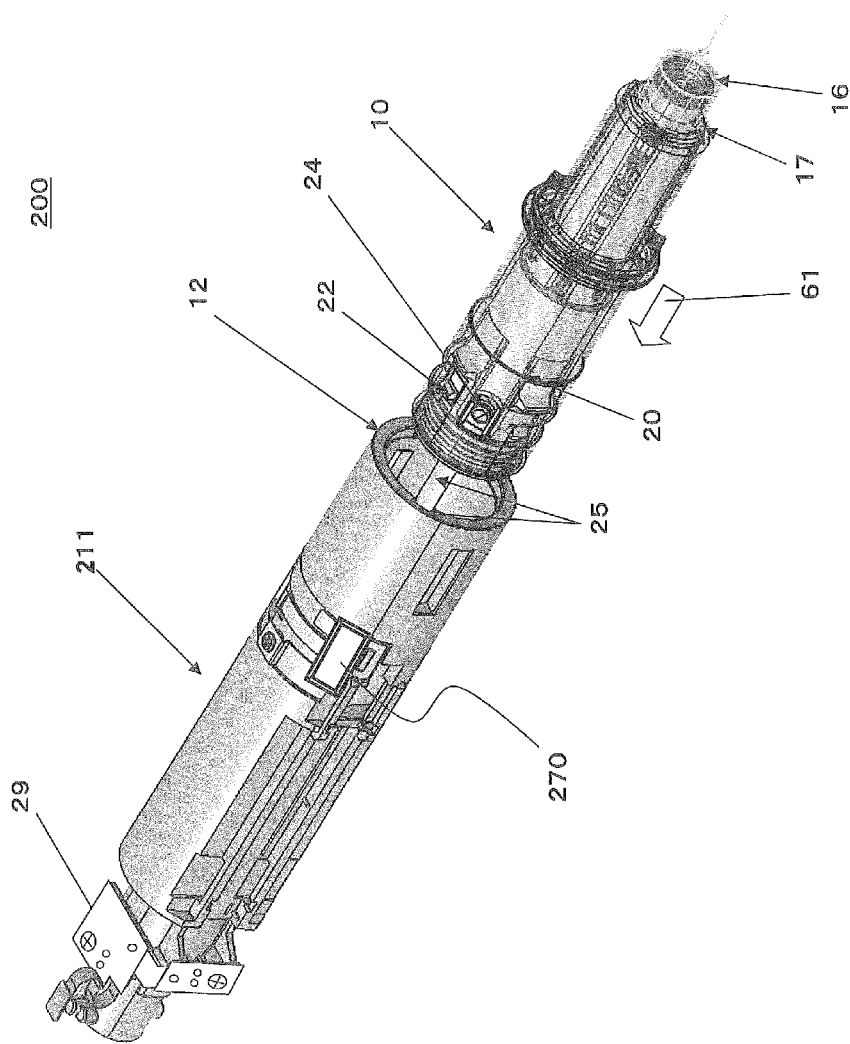
FIG. 21 is an oblique view of the movable portion in the interior of the pharmaceutical injection device pertaining to Embodiment 2.

As shown in FIG. 21, the pharmaceutical injection device 200 comprises an inner case 211 (an example of a movable member) that is mounted inside a main body case 1 (an example of a device main body) and has a detector 270 (an example of a first detector), a syringe holder 10 (an example of a pharmaceutical holding member) that is mounted on the front end side of the inner case 211, and a motor (an example of a driver; not shown). Just as in Embodiment 1, the syringe holder 10 is mounted by being inserted in the direction of the arrow 61 in FIG. 21 into the inner case 211. And just as in Embodiment 1, the motor drives the piston and drives the needle for insertion and withdrawal.

Figure 22:
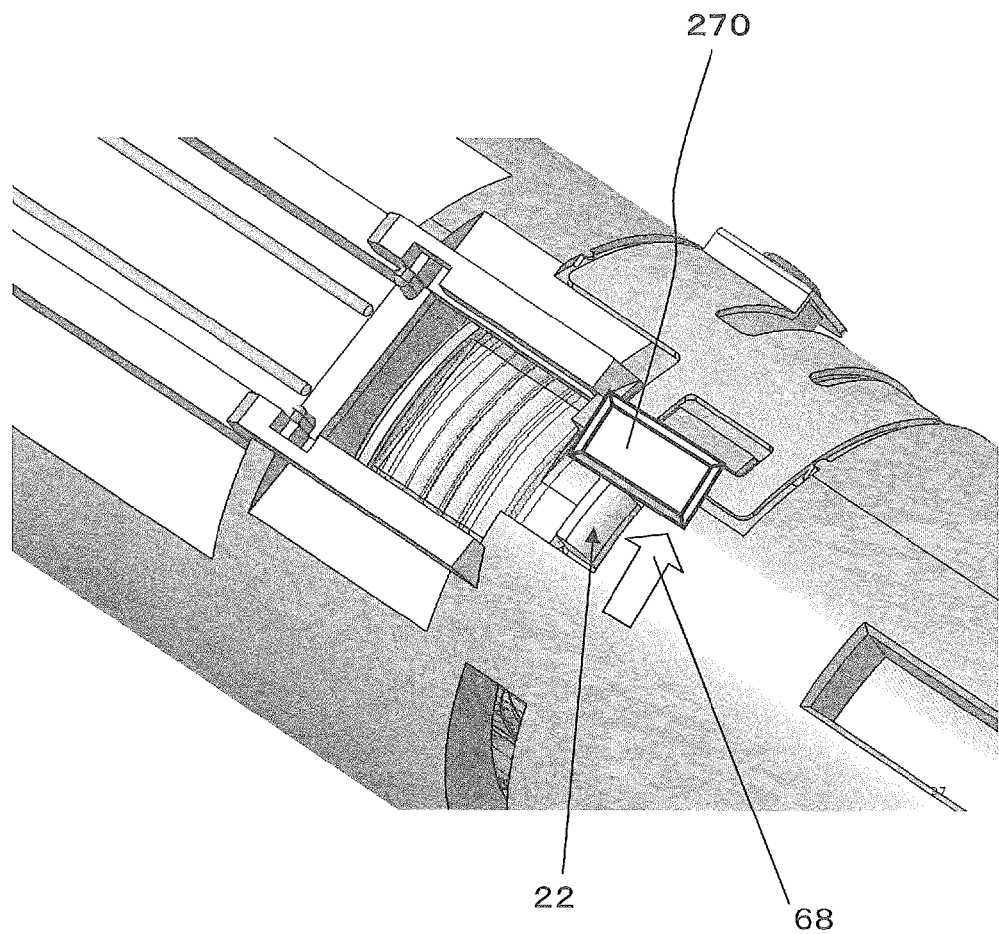
FIG. 22 is a detail view of the detector of the pharmaceutical injection device, and the surrounding area.

As shown in detail view in FIG. 22, the detector 270 is disposed near the protrusion 22 on the detector rod 19, and near the center part of the inner case 211. The detector 270 detects the mounting of the syringe holder 10 and/or the needle 16.

Figure 23:
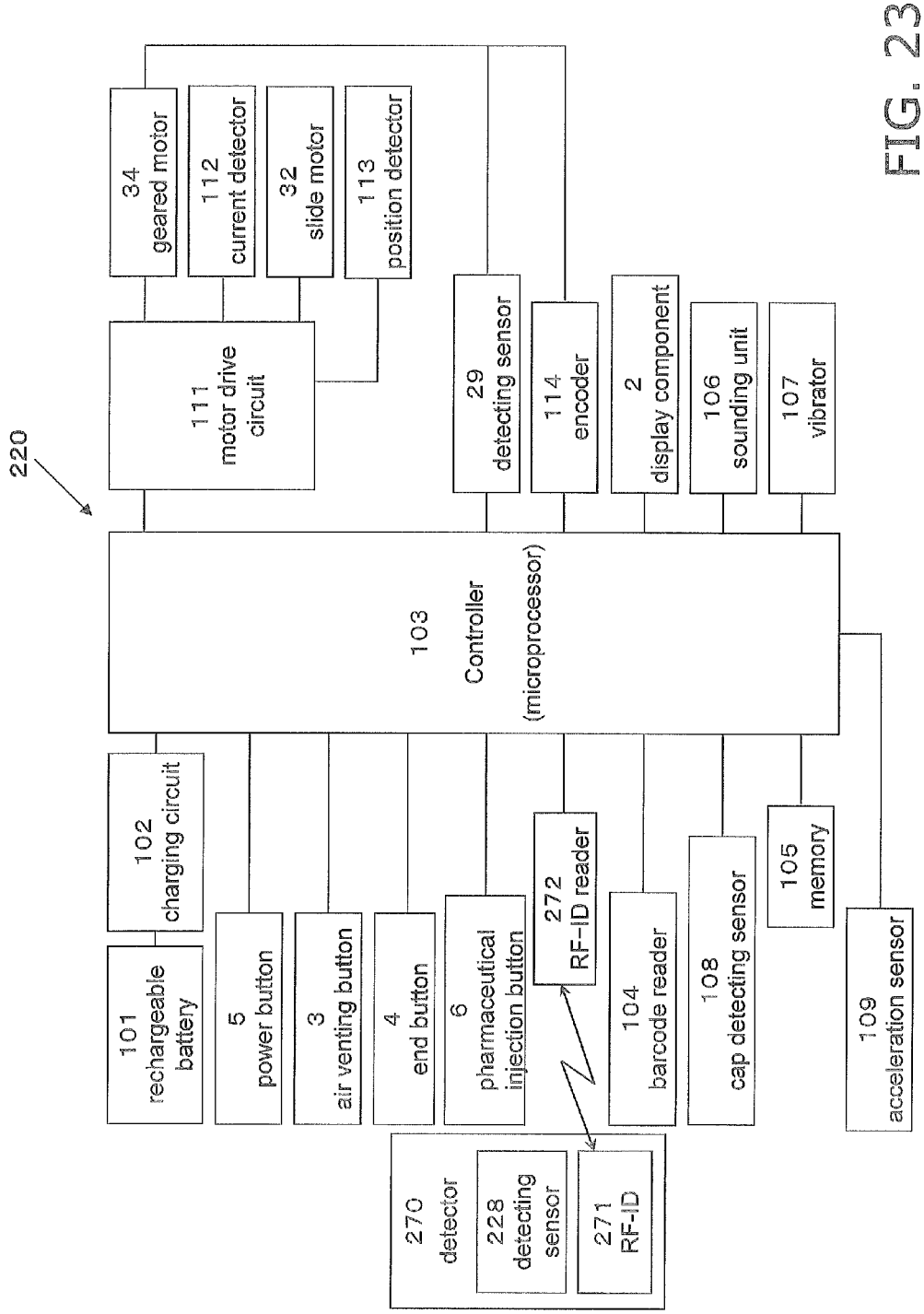
FIG. 23 is a diagram of the configuration of a control circuit in the pharmaceutical injection device.

FIG. 23 is a block diagram of a control circuit 220 of the pharmaceutical injection device 200 pertaining to Embodiment 2, and the surrounding components. As shown in this drawing, the detector 270 has a detecting sensor 228 and an RF-ID 271. An RF-ID reader 272 (an example of a receiver) that reads detection information from the RF-ID 271 is provided to the device main body (stationary side). The rest of the configuration of the control circuit is the same as in Embodiment 1.

The mounting of the syringe holder 10 to the inner case 211 is detected by utilizing the protrusions 22 on the syringe holder 10. That is, when the protrusions 22 move in the arrow 68 direction, this is detected by the detecting sensor 228 of the detector 270. The configuration of the detecting sensor 228 is the same as that in Embodiment 1 in that it is made up of a light emitting element such as an LED and a light receiving element such as a photodiode (optical elements). The detecting sensor 228 performs optical detection by using the protrusions 22 to block light between the light emitting element and the light receiving element. The signal detected by the detecting sensor 228 is stored in a memory in the RF-ID 271, and is read by the RF-ID reader 272 (FIG. 23) provided to the device main body (stationary side).

2.2 Processing by Pharmaceutical Injection Device 200

Figure 24:
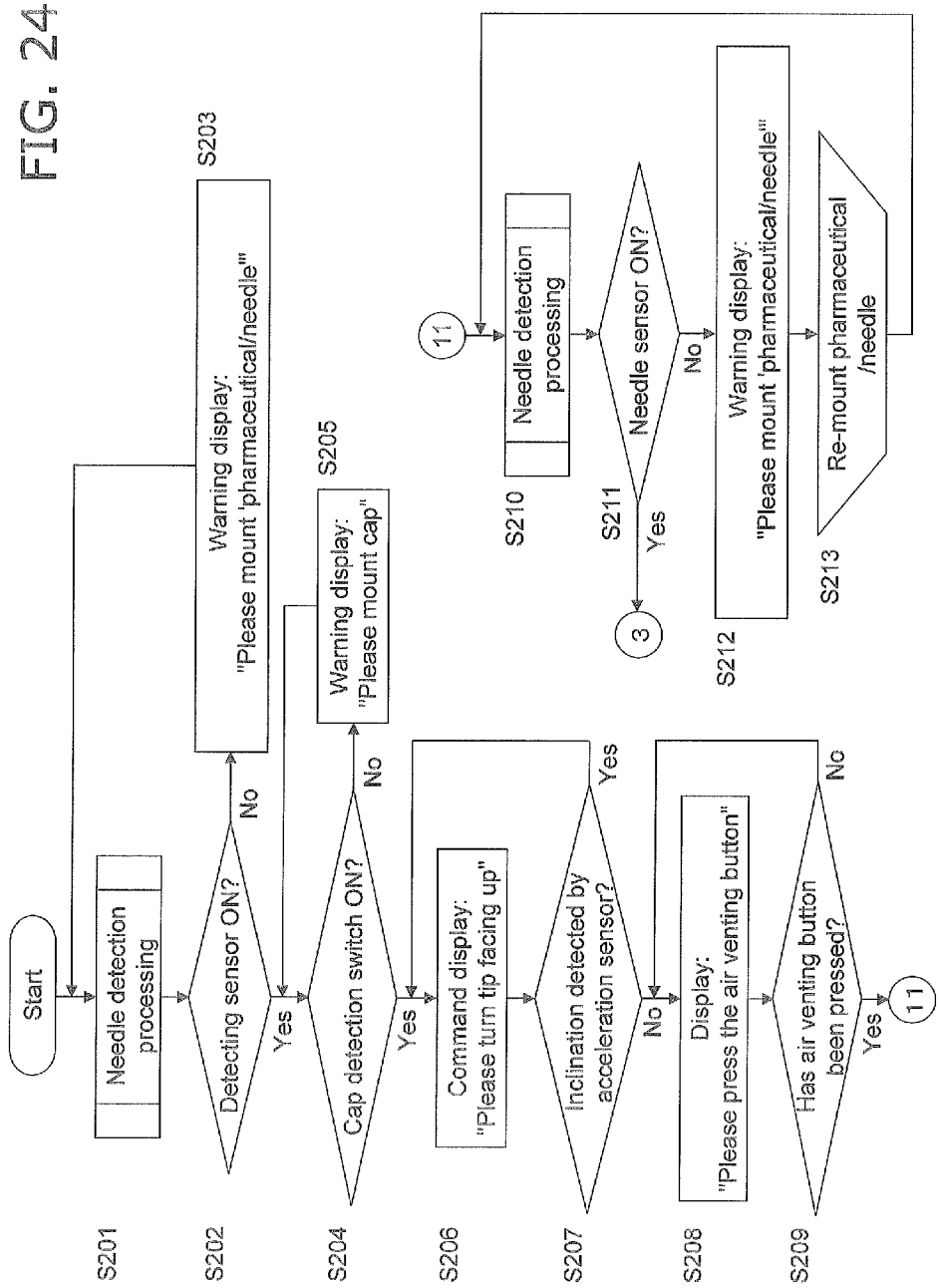
FIG. 24 is a flowchart of the processing performed by the pharmaceutical injection device.
Figure 25:
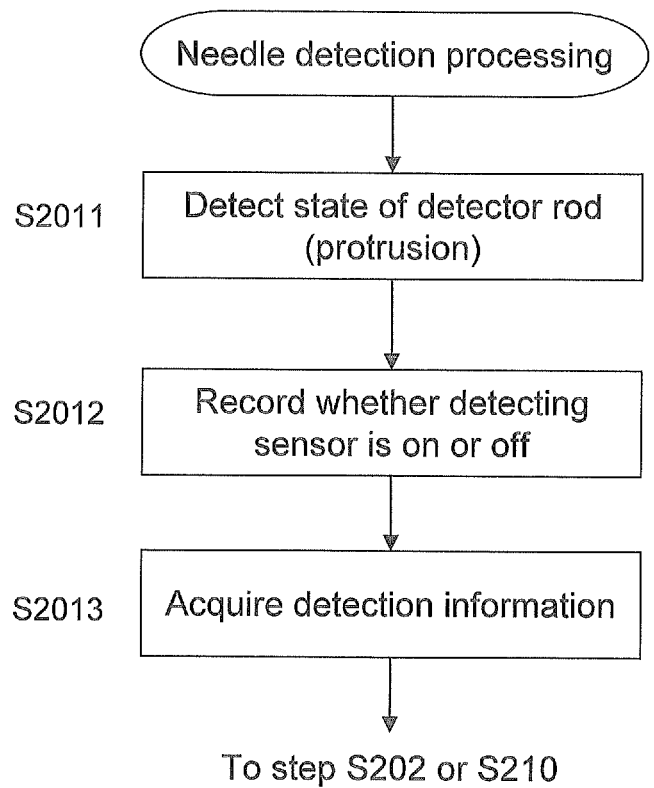
FIG. 25 is a flowchart of the processing performed by the pharmaceutical injection device.
Figure 26:
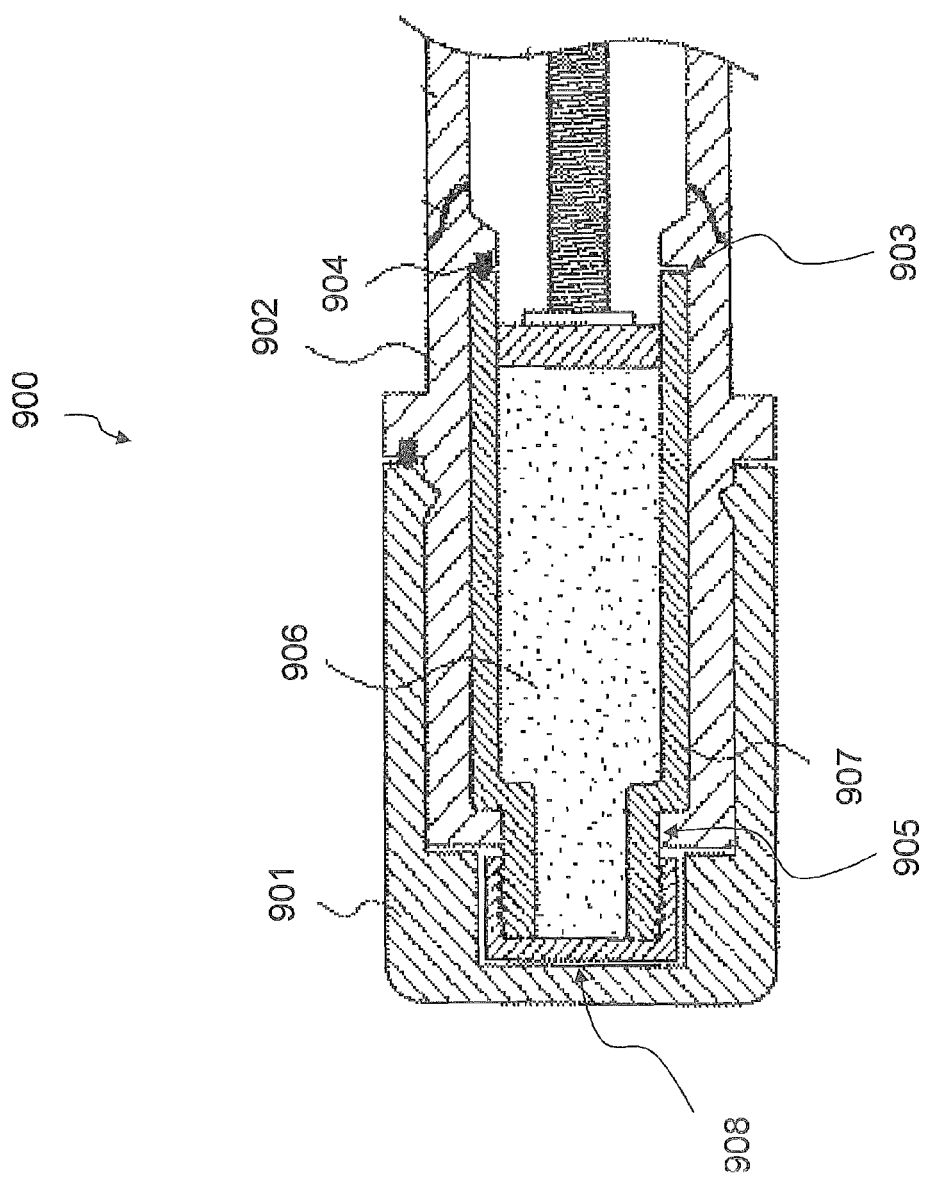
FIG. 26 is a partial cross section of a conventional pharmaceutical injection device.

FIGS. 24 and 25 are flowcharts of the operation in this embodiment, and show the air venting operation. The processing after air venting (the processing from step S112 onward in FIG. 17) is the same as that in Embodiment 1 above. In Embodiment 2, in a state in which the pharmaceutical syringe 50 has been installed and the needle 16 has been mounted in the syringe holder 10, and the syringe holder 10 has been mounted to the inner case 211 of the main body case 1, the user presses the power button 5 to turn on the pharmaceutical injection device 200.

2.2.1 Air Venting

Step S201: When the power button 5 is pressed, needle detection processing is first performed (see FIG. 25 for details), and the controller 103 detects whether or not the needle 16 (and the pharmaceutical syringe 50) has been mounted. That is, in place of step S101 from Embodiment 1 (see FIG. 16), the needle detection processing shown in FIG. 25 is performed in this embodiment.

Step S202: The controller 103 detects the mounting of the syringe holder 10 and/or the needle 16 on the basis of the detection signal from the RF-ID 271 in step S201. If the mounting is OK, the flow proceeds to step S204, but if the mounting is incorrect, the flow proceeds to step S203.

Step S203: A message recommending the mounting of the "pharmaceutical/needle" is displayed on the display component 2 of the main body case 1, and the system awaits the mounting of the syringe holder 10 and/or the needle 16 (returns to step S201).

Step S204: The mounting state of the cap 7 is detected by the cap detecting sensor 108. If the cap detecting sensor 108 is in its on state (if the cap has been mounted), the flow proceeds to step S206, but if it is in its off state (if the cap has not been mounted), the flow proceeds to step S205.

Step S205: A message recommending the mounting of the "cap" is displayed on the display component 2 of the main body case 1, and the system awaits the mounting of the cap 7 (returns to step S204).

Step S206: In a state in which the above preparations have been made, the flow proceeds to "air venting." A message is displayed on the display component 2 recommending the user to turn the distal end side of the main body case 1 (the side on which the cap 7 is mounted) upward.

Step S207: The inclination of the main body case 1 is detected by the acceleration sensor 109. If the acceleration sensor 109 detects that the angle between the ground and the vertical direction is within a specific range, the flow proceeds to step S208. Here, the distal end side of the main body case 1 only needs to be pointing slightly upward in order to perform air venting, but preferably the specific angle is defined to be a range of −45 to +45 degrees between the ground and the vertical direction. A range of −30 to +30 degrees is even more effective.

Step S208: In a state in which the distal end of the main body case 1 is facing upward, a message recommending the user to press the "air venting button" is displayed on the display component 2, and the system waits for the user to press the air venting button 3.

Step S209: When the pressing of the "air venting button" is detected, the flow proceeds to step S210.

Step S210: Needle detection processing is performed (see FIG. 25 for details), and the mounting of the syringe holder 10 and/or the needle 16 is detected.

Step S211: The controller 103 determines whether or not the mounting of the syringe holder 10 and/or the needle 16 was detected, on the basis of the detection signal from the RF-ID 271 in step S210. If the mounting is OK, the flow proceeds to step S112 in FIG. 17, but if the mounting is incorrect, the flow proceeds to step S212.

Step S212: A message recommending the mounting of the syringe holder 10 and/or the needle 16 is displayed on the display component 2.

Step S213: The user mounts the syringe holder 10 and/or the needle 16, and the mounting state is again detected (returns to step S210).

2.2.2. Needle Detection Processing

Next, the needle detection processing in steps S201 and S210 in FIG. 24 will be described. The term "needle detection processing" here means that the mounting state of the syringe holder 10 and/or the needle 16 is detected.

Step S2011: The state (position) of the protrusions 22 on the detector rod 19 is detected by the detecting sensor 28. If the protrusions 22 on the detector rod 19 block the light from the light emitting element, it is determined to be an "on state," and if the light is not blocked, it is determined to be an "off state."

Step S2012: Detection information based on whether the detecting sensor 28 is on or off is recorded to the memory of the RF-ID 271.

Step S2013: The controller 103 receives the detection information of the RF-ID 271 from the RF-ID reader 272 on the device main body (stationary) side, the flow proceeds to step S202 in FIG. 25, and the detecting sensor 28 determines whether or not it indicates an on state.

2.3. Features of Embodiment 2

The pharmaceutical injection device 200 pertaining to this embodiment has the following features in addition to the features of Embodiment 1 above.

In Embodiment 2, since the detector 270 comprises the RF-ID 271, the detector 270 can be disposed in the middle, rather than at the end of the inner case 211, and there is no need for complicated relay parts, such as providing the slender detecting lever 27 to the inner case 11. Thus, when the syringe holder 10 has been mounted to the inner case 211, this mounting can be detected from the movement of just the protrusions 22 on the detector rod 19 of the syringe holder 10.

Also, since the RF-ID 271 is formed substantially in a plane, there are far fewer restrictions on parts and attachment locations, so this is advantageous from both a design and a cost standpoint.

Furthermore, the RF-ID 271 is wireless, and can be attached at any place on the device main body, so there are fewer restrictions on the product design, and since there is no need for extra members, a device that is more compact and less expensive can be obtained.

INDUSTRIAL APPLICABILITY

The pharmaceutical injection device of the present invention can be utilized as syringe for injecting a drug into a body, for example.

REFERENCE SIGNS LIST 1 main body case
2 display component
3 air venting button
4 end button
5 power button
6 pharmaceutical injection button
7 cap
8 confirmation window
9 opening
10 syringe holder
10*a* syringe holder cover
11 inner case
12 syringe holder mounting opening
14 piston
14*a* piston protrusion
15 piston insertion opening
16 needle
17 needle mount
18 needle cap
19 detector rod
19*a* rod main body
19*b* extension 19c prong
20 protrusion
20a inclined face
21, 23 opening
22 protrusion
24 protrusion
25 groove
27 detecting lever
27a reinforcing plate
27b inclined face
27c blocking plate
28, 29 detecting sensor
29a flexible cable
28b, 29b, light emitting element
28c, 29c light receiving element
30 position lever
30a blocking plate
31 spring
32 slide motor
33 slide screw
34 geared motor
35 encoder
36 joint
37 slide case
41 push shaft
42 coupling
42a coupling prong
50 pharmaceutical syringe
61 to 69 arrows
100 pharmaceutical injection device
200 pharmaceutical injection device
211 inner case
228 detecting sensor
270 detector
271 RF-ID
272 RF-ID reader

The invention claimed is:

1. A pharmaceutical injection device, comprising:
a main body;
a movable member provided in the main body, the movable member being mounted movably in a lengthwise direction of the main body;
a pharmaceutical holding member mounted to the movable member and including a needle mount to which an injection needle is mounted on one end, the pharmaceutical holding member being configured to house a pharmaceutical syringe containing a drug to be injected into a body;
a first detector provided to the movable member and being configured to detect a mounting of an injection needle on the needle mount; and
a detection member configured to move with respect to the movable member when an injection needle has been mounted to the needle mount of the pharmaceutical holding member,
wherein the first detector is provided on an opposite side of the movable member from the needle mount,
the first detector detects the mounting of the injection needle on the needle mount by movement of the detection member in a lengthwise direction of the movable member,
the detection member includes a first detection member and a second detection member that is movable by contact with the first detection member,
the first detector detects movement of the second detection member,
the first detection member includes a protrusion,
the second detection member includes a slender projection extending in the lengthwise direction of the main body,
the protrusion comes into contact with the projection by moving in a direction away from the needle mount with respect to the movable member, and
the first detector detects movement of the projection.

2. The pharmaceutical injection device according to claim 1, wherein the first detector detects the mounting of an injection needle to the needle mount by detecting a mounting of the pharmaceutical holding member to the main body.

3. The pharmaceutical injection device according to claim 1, wherein the first detector includes a wireless tag, and the wireless tag transmits detection information from the first detector to a receiver provided to the main body.

4. The pharmaceutical injection device according to claim 1, wherein the first detector optically detects movement of the detection member.

5. The pharmaceutical injection device according to claim 1, wherein the first detector is disposed in a center of the movable member in a lengthwise direction of the movable member.

6. The pharmaceutical injection device according to claim 1, wherein the slender projection has a thick-walled part provided to an end surface on the protrusion side.

7. The pharmaceutical injection device according to claim 6, wherein the thick-walled part is formed extending from an end of the slender projection on the protrusion side toward the other end.

8. The pharmaceutical injection device according to claim 1, further comprising a movable member driver configured to move the movable member in the lengthwise direction of the main body in a state that the pharmaceutical holding member has been mounted to the movable member.

9. The pharmaceutical injection device according to claim 1, further comprising:
a piston driver configured to drive a piston provided inside the pharmaceutical holding member and inject a drug into the body; and
a second detector configured to detect that the piston is in an initial position.

10. The pharmaceutical injection device according to claim 9, wherein the first detector and the second detector are disposed in proximity to an end of the movable member on the opposite side from the needle mount.

11. The pharmaceutical injection device according to claim 9, wherein the first detector and the second detector are electrically connected by a flexible cable to a controller provided to the main body.

12. The pharmaceutical injection device according to claim 9, wherein the first detector is disposed at an angular position of 90 degrees or 180 degrees with respect to the second detector around a center axis of the movable member.

13. The pharmaceutical injection device according claim 1, wherein the first detector detects the mounting of an injection needle to the needle mount while the movable member is moving with respect to the main body or when the movable member is stopped.

14. The pharmaceutical injection device according to claim 1, further comprising a notification component configured to stop the movement of the movable member or issues a warning when no mounting of an injection needle to the needle mount is detected.

* * * * *